(12) United States Patent
Hillukka et al.

(10) Patent No.: US 11,246,658 B2
(45) Date of Patent: Feb. 15, 2022

(54) ABLATION CATHETER TIP

(71) Applicant: ST. JUDE MEDICAL, CARDIOLOGY DIVISION, INC., St. Paul, MN (US)

(72) Inventors: Brett A. Hillukka, Hanover, MN (US); Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 376 days.

(21) Appl. No.: 16/337,828

(22) PCT Filed: Aug. 30, 2017

(86) PCT No.: PCT/US2017/049264
§ 371 (c)(1),
(2) Date: Mar. 28, 2019

(87) PCT Pub. No.: WO2018/067248
PCT Pub. Date: Apr. 12, 2018

(65) Prior Publication Data
US 2020/0038100 A1  Feb. 6, 2020

Related U.S. Application Data

(60) Provisional application No. 62/404,013, filed on Oct. 4, 2016.

(51) Int. Cl.
*A61B 18/14* (2006.01)
*A61B 18/00* (2006.01)

(52) U.S. Cl.
CPC ............ *A61B 18/1492* (2013.01); *A61B 2018/00029* (2013.01); *A61B 2018/00077* (2013.01);
(Continued)

(58) Field of Classification Search
CPC ...... A61B 18/1492; A61B 2018/00029; A61B 2018/00077; A61B 2018/00101;
(Continued)

(56) References Cited

U.S. PATENT DOCUMENTS

| 3,674,014 A | 7/1972 | Tillander |
| 3,935,766 A | 2/1976 | Masters |

(Continued)

FOREIGN PATENT DOCUMENTS

| CN | 202776541 U | 3/2013 |
| CN | 103690237 A | 4/2014 |
| WO | 2016081650 A1 | 5/2016 |

OTHER PUBLICATIONS

Rozen, Guy et al., "Real Time Radiofrequeny Ablation Lesion Assessment with a Novel Technology Using Contact Force Sensing and Elaborate Catheter-Tissue Interface Temperature Measurement," HRS Presentation May 14, 2015.

(Continued)

*Primary Examiner* — Linda C Dvorak
*Assistant Examiner* — Lindsay Regan Lancaster
(74) *Attorney, Agent, or Firm* — Dykema Gossett PLLC

(57) ABSTRACT

Aspects of the present disclosure are directed to, for example, a high-thermal-sensitivity ablation catheter tip including a thermally-insulative ablation tip insert supporting a plurality of temperature sensors positioned within longitudinally-extending sensor channels and a radially-extending sensor channel within the tip insert. The sensor channels position the temperature sensors in thermal communication with a conductive shell that encapsulates, or essentially encapsulates, the ablation tip insert and the plurality of temperature sensors. Also disclosed is a method of controlling the temperature of an ablation catheter tip (Continued)

while creating a desired lesion using various ablative energies and energy delivery methodologies.

20 Claims, 29 Drawing Sheets

(52) U.S. Cl.
CPC ............... *A61B 2018/00101* (2013.01); *A61B 2018/00577* (2013.01); *A61B 2018/00642* (2013.01); *A61B 2018/00702* (2013.01); *A61B 2018/00797* (2013.01); *A61B 2018/00815* (2013.01); *A61B 2018/00821* (2013.01); *A61B 2218/002* (2013.01)

(58) Field of Classification Search
CPC ........... A61B 2018/00577; A61B 2018/00642; A61B 2018/00702; A61B 2018/00797; A61B 2018/00821; A61B 2218/002; A61B 2018/00095; A61B 2018/00666
See application file for complete search history.

(56) References Cited

U.S. PATENT DOCUMENTS

| | | |
|---|---|---|
| 4,809,713 A | 3/1989 | Grayzel |
| 4,945,912 A | 8/1990 | Langberg |
| 5,056,517 A | 10/1991 | Fenici |
| 5,057,105 A | 10/1991 | Malone |
| 5,176,144 A | 1/1993 | Yoshikoshi |
| 5,279,299 A | 1/1994 | Imran |
| 5,363,861 A | 11/1994 | Edwards |
| 5,378,230 A | 1/1995 | Mahurkar |
| 5,542,938 A | 8/1996 | Avellanet |
| 5,545,200 A | 8/1996 | West |
| 5,662,647 A | 9/1997 | Crow |
| 5,681,280 A | 10/1997 | Rusk et al. |
| 5,688,267 A | 11/1997 | Panescu et al. |
| 5,706,827 A | 1/1998 | Ehr |
| 5,755,790 A | 5/1998 | Chevillon et al. |
| 5,769,847 A | 6/1998 | Panescu et al. |
| 5,782,810 A | 7/1998 | O'Donnell |
| 5,788,713 A | 8/1998 | Dubach |
| 5,810,804 A | 9/1998 | Gough et al. |
| 5,849,028 A | 12/1998 | Chen |
| 5,893,885 A | 4/1999 | Webster |
| 5,911,720 A | 6/1999 | Bourne |
| 5,951,471 A | 9/1999 | de la Rama |
| 5,957,961 A | 9/1999 | Maguire et al. |
| 5,979,180 A | 10/1999 | Sherman |
| 6,001,095 A | 12/1999 | de la Rama |
| 6,015,414 A | 1/2000 | Werp |
| 6,045,550 A | 4/2000 | Simpson et al. |
| 6,068,641 A | 5/2000 | Varsseveld |
| 6,113,591 A | 9/2000 | Whayne et al. |
| 6,123,702 A | 9/2000 | Swanson et al. |
| 6,126,647 A | 10/2000 | Posey |
| 6,162,184 A | 12/2000 | Swanson et al. |
| 6,171,275 B1 | 1/2001 | Webster |
| 6,185,448 B1 | 2/2001 | Borovsky |
| 6,190,180 B1 | 2/2001 | Purington et al. |
| 6,197,021 B1 | 3/2001 | Panescu et al. |
| 6,208,881 B1 | 3/2001 | Champeau |
| 6,217,573 B1 | 4/2001 | Webster |
| 6,233,479 B1 | 5/2001 | Strommer |
| 6,235,024 B1 | 5/2001 | Tu |
| 6,245,061 B1 | 6/2001 | Panescu et al. |
| 6,251,134 B1 | 6/2001 | Alt |
| 6,273,876 B1 | 8/2001 | Klima |
| 6,292,678 B1 | 9/2001 | Hall |
| 6,322,584 B2 | 11/2001 | Ingle et al. |
| 6,356,790 B1 | 3/2002 | Maguire |
| 6,385,472 B1 | 5/2002 | Hall |
| 6,405,067 B1 | 6/2002 | Mest et al. |
| 6,425,894 B1 | 7/2002 | Brucker et al. |
| 6,464,632 B1 | 10/2002 | Taylor |
| 6,475,223 B1 | 11/2002 | Werp |
| 6,477,396 B1 | 11/2002 | Mest et al. |
| 6,493,590 B1 | 12/2002 | Wessman |
| 6,498,944 B1 | 12/2002 | Ben-Haim et al. |
| 6,500,172 B1 | 12/2002 | Panescu |
| 6,524,303 B1 | 2/2003 | Garibaldi |
| 6,544,270 B1 | 4/2003 | Zhang |
| 6,592,580 B1 | 7/2003 | Stockert |
| 6,605,087 B2 | 8/2003 | Swartz |
| 6,611,699 B2 | 8/2003 | Messing |
| 6,662,034 B2 | 12/2003 | Segner |
| 6,669,692 B1 | 12/2003 | Nelson |
| 6,690,963 B2 | 2/2004 | Ben-Haim |
| 6,730,082 B2 | 5/2004 | Messing |
| 6,733,497 B2 | 5/2004 | Messing |
| 6,740,083 B2 | 5/2004 | Messing |
| 6,755,816 B2 | 6/2004 | Ritter |
| 6,780,183 B2 | 8/2004 | Jimenez, Jr. |
| 6,788,967 B2 | 9/2004 | Ben-Haim et al. |
| 6,980,843 B2 | 12/2005 | Eng |
| 7,137,395 B2 | 11/2006 | Fried |
| 7,197,354 B2 | 3/2007 | Sobe |
| 7,207,989 B2 | 4/2007 | Pike, Jr. |
| 7,211,082 B2 | 5/2007 | Hall |
| 7,263,397 B2 | 8/2007 | Hauck |
| 7,276,044 B2 | 10/2007 | Ferry |
| 7,280,863 B2 | 10/2007 | Shachar |
| 7,386,339 B2 | 6/2008 | Strommer |
| 7,341,063 B2 | 11/2008 | Garibaldi |
| 7,536,218 B2 | 5/2009 | Govari |
| 7,594,913 B2 | 9/2009 | Ormsby et al. |
| 7,655,003 B2 | 2/2010 | Lorang et al. |
| 7,742,795 B2 * | 6/2010 | Stone ................ A61B 18/1492 600/381 |
| 7,766,907 B2 | 8/2010 | Dando et al. |
| 7,998,141 B2 | 8/2011 | Wittkampf et al. |
| 8,348,937 B2 | 1/2013 | Wang et al. |
| 8,414,579 B2 | 4/2013 | Kim et al. |
| 8,845,633 B2 | 9/2014 | Wang et al. |
| 9,532,828 B2 | 1/2017 | Condie et al. |
| 9,788,891 B2 | 10/2017 | Christian et al. |
| 2001/0012956 A1 | 8/2001 | Behl |
| 2001/0047129 A1 | 11/2001 | Hall et al. |
| 2002/0022834 A1 | 2/2002 | Simpson et al. |
| 2002/0058866 A1 | 5/2002 | Segner |
| 2002/0072662 A1 | 6/2002 | Hall |
| 2003/0125752 A1 | 7/2003 | Werp |
| 2003/0176766 A1 | 9/2003 | Long |
| 2003/0216639 A1 | 11/2003 | Gilboa et al. |
| 2004/0015215 A1 | 1/2004 | Fredricks |
| 2004/0019447 A1 | 1/2004 | Shachar |
| 2004/0158142 A1 | 8/2004 | Hall |
| 2004/0204671 A1 | 10/2004 | Stubbs |
| 2004/0231683 A1 | 11/2004 | Eng |
| 2004/0242995 A1 | 12/2004 | Maschke |
| 2004/0243143 A1 | 12/2004 | Corcoran |
| 2004/0267106 A1 | 12/2004 | Segner |
| 2005/0004563 A1 | 1/2005 | Racz |
| 2005/0054989 A1 | 3/2005 | McGuckin, Jr. |
| 2005/0070894 A1 | 3/2005 | McClurken |
| 2005/0096589 A1 | 5/2005 | Shachar |
| 2005/0174004 A1 | 8/2005 | Takehara |
| 2005/0197633 A1 | 9/2005 | Schwartz |
| 2005/0222560 A1 | 10/2005 | Kimura et al. |
| 2005/0245846 A1 | 11/2005 | Casey |
| 2005/0272975 A1 | 12/2005 | McWeeney |
| 2006/0064123 A1 | 3/2006 | Bonnette |
| 2006/0114088 A1 | 6/2006 | Shachar |
| 2006/0116633 A1 | 6/2006 | Shachar |
| 2006/0116634 A1 | 6/2006 | Shachar |
| 2006/0149192 A1 | 7/2006 | Deniega |
| 2006/0200191 A1 | 9/2006 | Zadno-Azizi |
| 2006/0287650 A1 | 12/2006 | Cao |
| 2007/0016006 A1 | 1/2007 | Shachar |
| 2007/0016131 A1 | 1/2007 | Munger |
| 2007/0066878 A1 | 3/2007 | Worley |
| 2007/0073268 A1 | 3/2007 | Goble |

(56) References Cited

U.S. PATENT DOCUMENTS

| | | |
|---|---|---|
| 2007/0197891 A1 | 8/2007 | Shachar |
| 2007/0270791 A1 | 11/2007 | Wang et al. |
| 2008/0027313 A1 | 1/2008 | Shachar |
| 2008/0039705 A1 | 2/2008 | Viswanathan |
| 2008/0045943 A1 | 2/2008 | Wittkampf |
| 2008/0091193 A1 | 4/2008 | Kauphusman |
| 2008/0097429 A1 | 4/2008 | McClurken |
| 2008/0161797 A1 | 7/2008 | Wang |
| 2008/0249395 A1 | 10/2008 | Shachar |
| 2008/0255642 A1 | 10/2008 | Zarins |
| 2008/0297287 A1 | 12/2008 | Malackowski et al. |
| 2008/0319418 A1 | 12/2008 | Chong |
| 2009/0163916 A1 | 6/2009 | Paul |
| 2009/0171272 A1 | 7/2009 | Tegg |
| 2009/0171348 A1 | 7/2009 | Guo |
| 2009/0234347 A1 | 9/2009 | Treat et al. |
| 2009/0259222 A1 | 10/2009 | Wang et al. |
| 2009/0306653 A1 | 12/2009 | Anderson et al. |
| 2009/0306655 A1 | 12/2009 | Stangenes |
| 2010/0174177 A1 | 7/2010 | Wu |
| 2011/0160726 A1* | 6/2011 | Ingle ............... A61B 18/1492 606/49 |
| 2011/0224667 A1* | 9/2011 | Koblish ............ A61B 18/1492 606/41 |
| 2011/0264089 A1 | 10/2011 | Zirkle et al. |
| 2012/0157991 A1 | 6/2012 | Christian |
| 2012/0165812 A1 | 6/2012 | Christian |
| 2012/0245576 A1 | 9/2012 | Epstein et al. |
| 2012/0310080 A1 | 12/2012 | Cunningham et al. |
| 2013/0237977 A1 | 9/2013 | McCarthy et al. |
| 2014/0171821 A1 | 6/2014 | Govari et al. |
| 2014/0171936 A1* | 6/2014 | Govari ............... A61B 18/1492 606/34 |
| 2014/0187893 A1 | 7/2014 | Clark et al. |
| 2014/0276052 A1 | 9/2014 | Rankin et al. |
| 2015/0025526 A1 | 1/2015 | Hua et al. |
| 2015/0066003 A1 | 3/2015 | Epstein et al. |
| 2015/0105701 A1 | 4/2015 | Mayer et al. |
| 2015/0289932 A1 | 10/2015 | Tegg et al. |
| 2015/0297292 A1* | 10/2015 | Sutermeister ...... A61B 18/1492 606/41 |
| 2016/0143690 A1 | 5/2016 | Schultz et al. |
| 2016/0192982 A1 | 7/2016 | Just et al. |
| 2016/0276739 A1* | 9/2016 | Buesseler ............... H01Q 7/06 |
| 2016/0287312 A1 | 10/2016 | Tegg et al. |
| 2016/0287326 A1 | 10/2016 | Tegg et al. |
| 2016/0128765 A1 | 12/2016 | Schultz |
| 2017/0042449 A1 | 2/2017 | Deno et al. |
| 2018/0092688 A1 | 4/2018 | Tegg |
| 2018/0092689 A1 | 4/2018 | Tegg et al. |

OTHER PUBLICATIONS

Mass Device, Advanced Cardiac Thereapeutics touts 1st-in-human trial for RF ablation tech, Jan. 28, 2016; pp. 1-2.

* cited by examiner

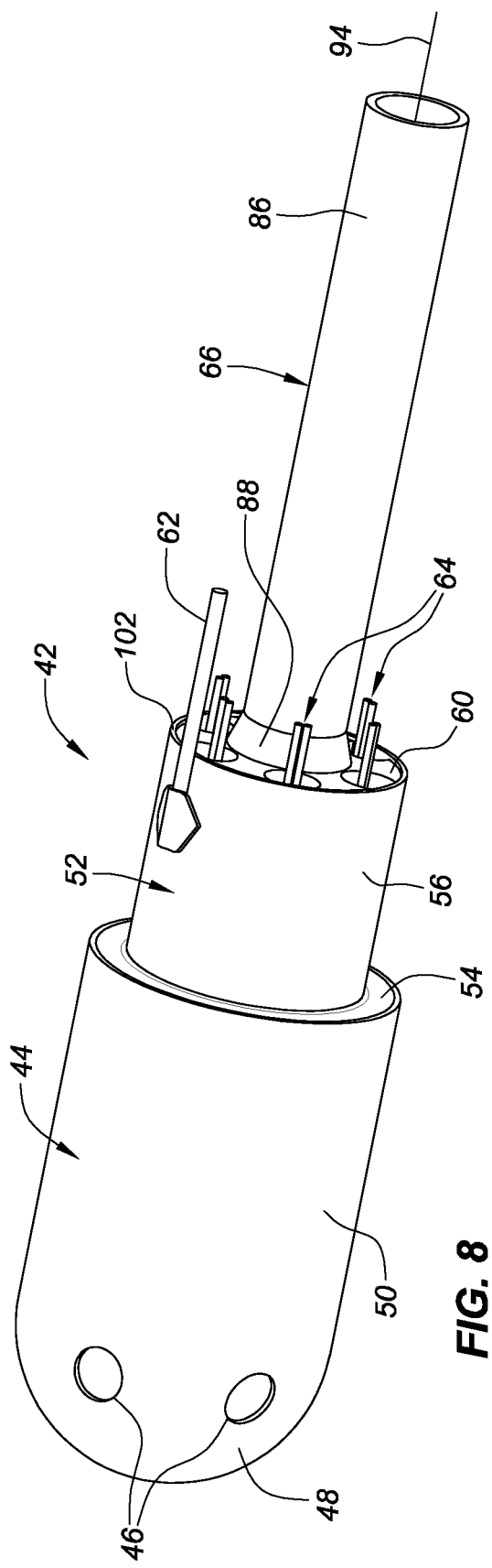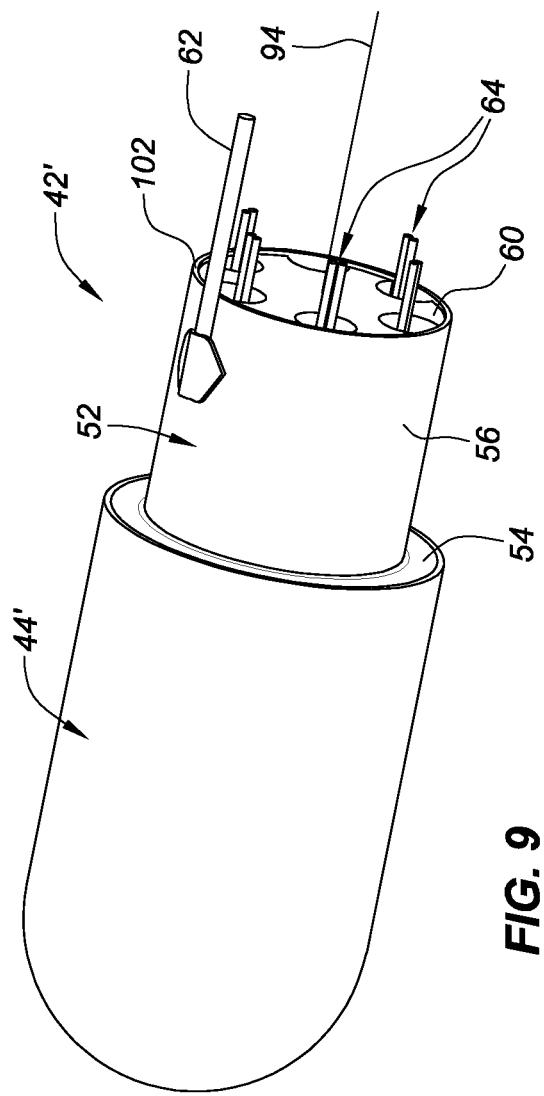

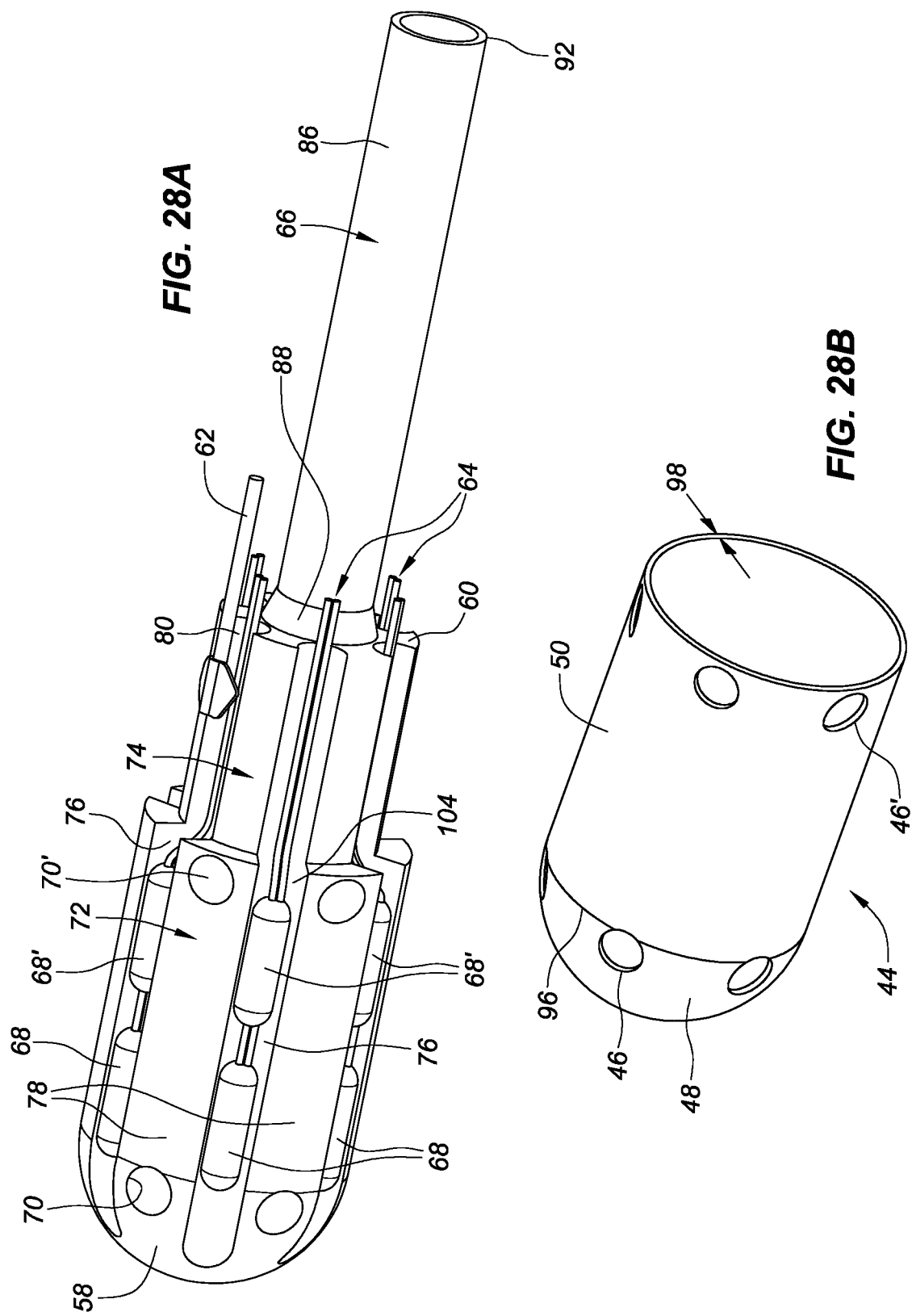

ABLATION CATHETER TIP

CROSS-REFERENCE TO RELATED APPLICATION

This application claims the benefit of U.S. provisional application No. 62/404,013, filed 4 Oct. 2016, which is hereby incorporated by reference as though fully set forth herein.

This application is related to U.S. application Ser. No. 15/088,036, filed 31 Mar. 2016 (the '036 application), now pending, which claims the benefit of U.S. provisional application No. 62/141,066, filed 31 Mar. 2015 (the '066 application). This application is also related to U.S. application Ser. No. 15/088,052, filed 31 Mar. 2016 (the '052 application), now pending, which claims the benefit of U.S. provisional application No. 62/198,114, filed 28 Jul. 2015 (the '114 application). This application is also related to U.S. provisional application No. 62/404,038, filed 4 Oct. 2016 (the '038 application) and U.S. provisional application No. 62/404,060, filed 4 Oct. 2016 (the '060 application). The '036, '066, '052, '114, '038, and '060 applications are all hereby incorporated by reference as though fully set forth herein.

BACKGROUND OF THE DISCLOSURE a. Field

The present disclosure relates to low thermal mass ablation catheter tips (also known as high-thermal-sensitivity catheter tips) and to systems for controlling the delivery of RF energy to such catheters during ablation procedures.

b. Background

RF generators used during catheter ablation procedures are often set in a "temperature control" mode, and the power is initially set to a value that is sufficiently high (for example, 35 Watts) to create lesions in tissue and the tip temperature is set to, for example, 40° C. As soon as the tip reaches 40° C., the power is titrated down to a lower power setting such as, for example, 15 Watts to maintain the 40° C. target temperature. This can, however, create problems in that such lower power settings (e.g., 15 Watts) may be too low to create lesions that are deep enough to be effective for treating abnormal heart rhythms.

The foregoing discussion is intended only to illustrate the present field and should not be taken as a disavowal of claim scope.

BRIEF SUMMARY OF THE DISCLOSURE

It is desirable to be able to control the delivery of RF energy to a catheter to enable the creation of lesions in tissue by keeping the generator power setting sufficiently high to form adequate lesions while mitigating against overheating of tissue.

Various embodiments of the present disclosure are directed to a high-thermal-sensitivity ablation catheter tip. The ablation catheter tip including an electrically-conductive housing, a thermally-insulative tip insert, a plurality of thermal sensors, and a wired or wireless communication pathway. The electrically-conductive housing includes a conductive shell that surrounds at least a portion of the tip insert, and the thermally-insulative tip insert includes a plurality of longitudinally-extending sensor channels and a radially-extending sensor channel. The plurality of thermal sensors are in thermal communication with the conductive shell and provide directional temperature feedback. Each of the thermal sensors are circumferentially distributed around the tip insert in the plurality of longitudinally extending sensor channels and the radially-extending sensor channel. The wired or wireless communication pathway is communicatively connected to the plurality of thermal sensors and reports the directional temperature feedback to an ablation control system. In further more specific embodiments, the thermal sensors that are circumferentially distributed around the tip insert in the plurality of longitudinally extending sensor channels are radially offset relative to the thermal sensors that are circumferentially distributed around the tip insert in the radially-extending sensor channel.

Some embodiments of the present disclosure are directed to ablation tips for an ablation catheter. The ablation tip includes a thermally and electrically conductive housing, a thermally-insulative tip insert, and a plurality of thermal sensors. The thermally and electrically conductive housing includes a conductive shell that comprises an inner surface, and surrounds at least a portion of the tip insert. The thermally-insulative tip insert includes a plurality of longitudinally-extending sensor channels and a plurality of longitudinally-extending lead wire channels positioned between the plurality of longitudinally-extending sensor channels. The plurality of thermal sensors are circumferentially distributed around the tip insert in the plurality of longitudinally extending sensor channels and in thermally-transmissive contact with the inner surface of the conductive shell. Each of the plurality of thermal sensors receive and report temperature feedback received through the conductive shell via the wired or wireless communication pathway which is communicatively connected to the plurality of thermal sensors and an ablation control system.

Yet other embodiments of the present disclosure are directed to an ablation catheter tip having high-thermal-sensitivity. The ablation catheter tip includes a thermally-insulative ablation tip insert, a conductive shell, and a shank. The thermally-insulative ablation tip insert includes a first portion and a second portion, where the first portion of the tip insert includes a plurality of longitudinally-extending sensor channels and a radially-extending sensor channel. The insert supports a plurality of temperature sensors circumferentially distributed around the tip insert in the plurality of longitudinally extending sensor channels and the radially-extending sensor channel. The temperature sensors form proximal and distal circumferential rings. The conductive shell includes a shell distal end portion and a shell proximal end portion, where the conductive shell is adapted to fit around the first portion of the insert in thermally-conductive contact with the plurality of temperature sensors in the proximal and distal circumferential rings. The shank is adapted to cover the second portion of the insert, whereby the conductive shell and the shank are conductively connected and together effectively encase the ablation tip insert.

The foregoing and other aspects, features, details, utilities, and advantages of the present disclosure will be apparent from reading the following description and claims, and from reviewing the accompanying drawings.

DESCRIPTION OF THE DRAWINGS

Various example embodiments may be more completely understood in consideration of the following detailed description in connection with the accompanying drawings, in which:

FIG. 8 is a fragmentary, isometric view of various components comprising the distal end of an ablation catheter that could be used with the pulsed RF control systems disclosed herein.

FIG. 9 is similar to FIG. 8, but depicts components of the distal end of a non-irrigated catheter that could be used in combination with the pulsed RF control systems disclosed herein.

FIG. 28A is most similar to FIG. 20, but depicts an embodiment of the tip insert on which both distal and proximal temperature sensors are mounted.

FIG. 28B is an isometric view of a conductive shell for assembly over the tip insert of FIG. 28A, consistent with various aspects of the present disclosure.

Figure 1:
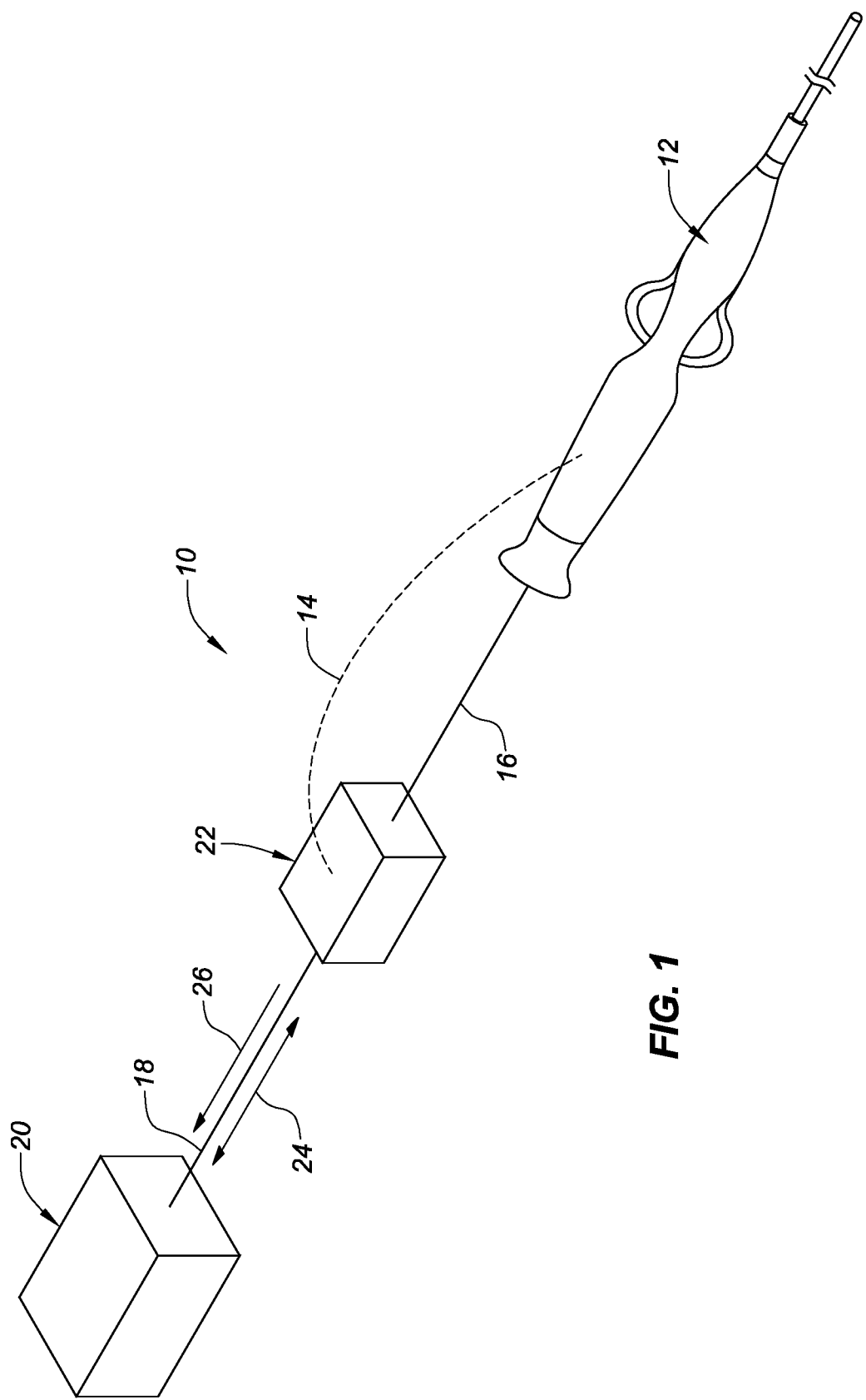
FIG. 1 is a highly-schematic representation of one embodiment of a system for delivering pulsed RF energy during catheter ablation, showing possible communication pathways between primary components in this embodiment.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

FIG. 1 is a highly-schematic representation of one embodiment of a system 10 for delivering pulsed RF energy to an ablation catheter 12 during catheter ablation, showing possible communication pathways 14, 16, 18 between primary components in this embodiment. This figure depicts a generator 20 operatively connected to a pulse control box 22, which is operatively connected to the ablation catheter 12. In this figure, a number of possible wired and/or wireless communication pathways are shown. For example, a dashed line 14 represents temperature feedback from the catheter to the pulse control box 22 of readings from at least one temperature sensor mounted in the tip of the catheter 12. In this embodiment, and in all of the embodiments described herein, the catheter may comprise multiple thermal sensors (for example, thermocouples or thermistors), as described further below. If the catheter comprises multiple temperature sensors mounted in its tip region, the feedback shown in FIG. 1 from the catheter to the pulse control box may be, for example, the highest reading from among all of the individual temperature sensor readings, or it may be, for example, an average of all of the individual readings from all of the temperature sensors.

In FIG. 1, two communication options, represented by double-headed arrow 24 and single-headed arrow 26, are shown for delivering information to the generator 20 or exchanging information between the pulse control box 22 and the generator 20. The communication pathway 18 between the generator 20 and the pulse control box 22 could comprise, for example, multiple, separate electrical connection (not separately shown) between the generator 20 and the pulse control box 22. One of these communication lines could be, for example, a separate (possibly dedicated) line for communicating to the generator the highest temperature measured by any of a plurality of temperature sensors mounted in the catheter tip. This could be used to trigger a temperature-based shutdown feature in the generator for patient safety. In other words, the temperature reading or readings from the catheter may be sent to the pulse control box, which may then feed the highest temperature reading to the generator so that the generator can engage its safety features and shut down if the temperature reading appears to be getting undesirably or unsafely high.

In an alternative configuration, the generator 20 "thinks" it is delivering RF energy to the catheter, but that energy is being delivered instead to the pulse control box 22. The pulse control box then determines, based upon the temperature feedback that it receives from the catheter, whether to drive the catheter at the power level coming from the generator or, alternatively, to pulse the delivery of RF energy to the catheter tip. In this configuration, the generator may be blind to the fact that the pulse control box 22 is determining whether to send power to the catheter tip or to momentarily suspend delivery of energy to the catheter tip as a means of effectively controlling tissue temperature by monitoring and controlling catheter tip temperature.

Figure 2:
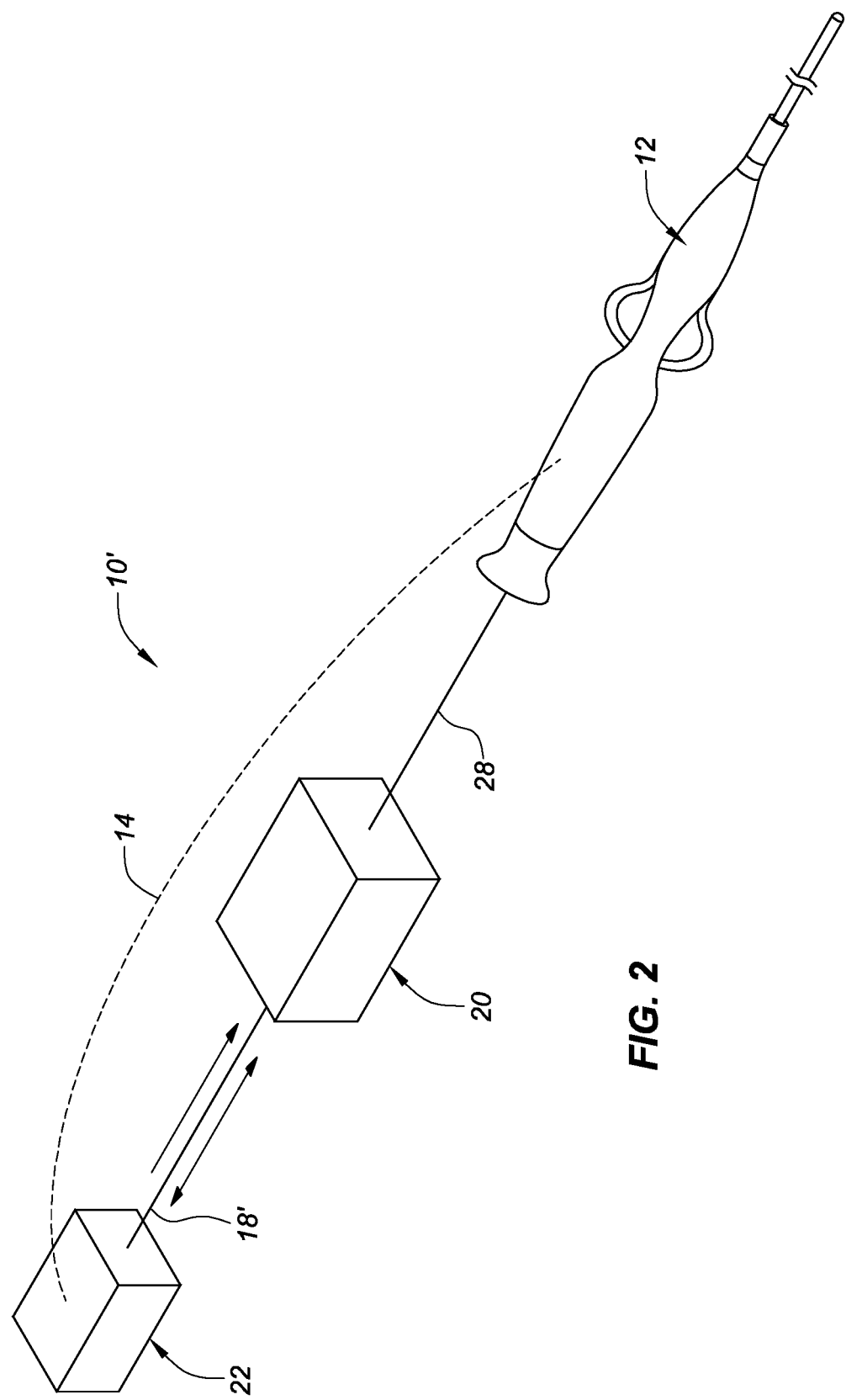
FIG. 2 is similar to FIG. 1, but depicts the components arranged in a slightly different configuration in an alternative embodiment of a system for delivering pulsed RF energy during catheter ablation.

FIG. 2 is similar to FIG. 1, but depicts the components arranged in a slightly different configuration in an alternative embodiment of a system 10' for delivering pulsed RF energy during catheter ablation. In FIG. 2, the pulse control box 22 is again receiving temperature feedback from the catheter 12 along communication pathway 14. However, in FIG. 2, the pulse control box 22 is "telling" the generator (e.g., along communication pathway 18') to switch "off" and "on" based on the sensed temperature from the catheter 12. The generator 20 then delivers pulsed RF energy to the catheter 12 via communication pathway 28. In this system 10' for delivering pulsed RF energy, as in the system 10 depicted in FIG. 1 and discussed herein, the power can remain at a desired power level (e.g., 50 or 60 Watts) rather than being reduced to an ineffective level when excessive temperature is sensed by the catheter tip. In particular, rather than reducing the power to control temperature, the power is delivered in a pulsed manner; and it is the control of the energy pulses, including control of the length of the time gaps between pulses, that is used to control the tip temperature as a surrogate for controlling the tissue temperature. As a further alternative for how the system 10' depicted in FIG. 2 may operate, the generator 20 may receive temperature feedback via communication pathway 28 and then pass temperature feedback information to the pulse control box 22, which would then control the generator 20 as described above.

Figure 3:
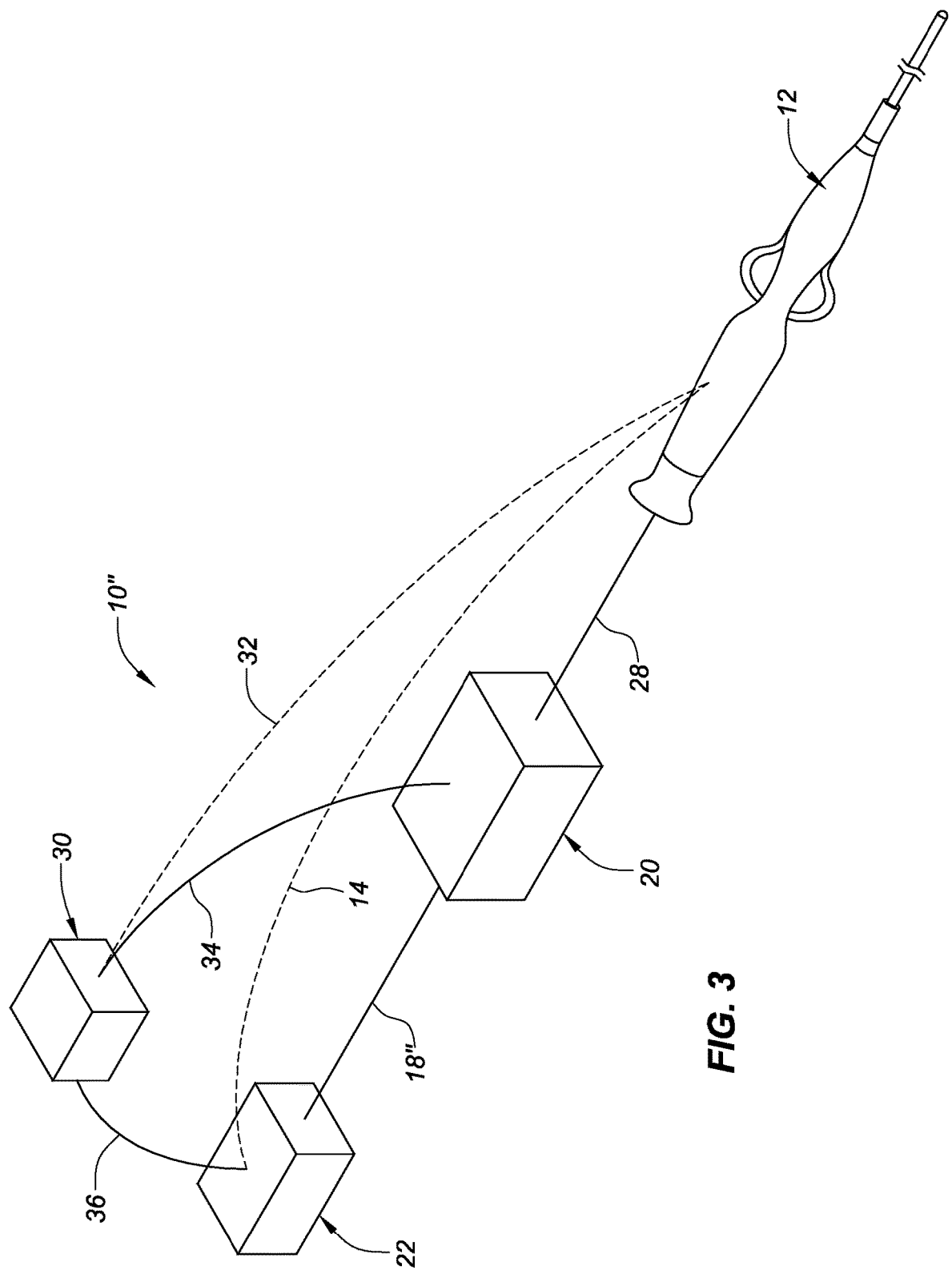
FIG. 3 is similar to FIGS. 1 and 2, but depicts a system with a dedicated central processing unit interfacing with the components also depicted in FIGS. 1 and 2.

FIG. 3 is similar to FIGS. 1 and 2, but depicts a system 10" with a dedicated central processing unit (CPU) 30 interfacing with the components 12, 20, 22 also depicted in FIGS. 1 and 2. As shown in this figure, a dedicated CPU is among the components in the system 10" for delivering pulsed RF energy during ablation. This figure also shows a number of potential communication pathways between and among the various components, including, for example, a temperature feedback pathway 32 between the catheter and the CPU, the temperature feedback pathway 14 between the catheter and the pulse control box 22, a communication pathway 34 between the generator 20 and the CPU 30, a communication pathway 18" between the generator and the pulse control box, the communication pathway 28 between the generator 20 and the catheter 12, and a communication pathway 36 between the CPU and the pulse control box. The following are various possible combinations of pathways that could be used, assuming the overall system comprises at least the four components 12, 20, 22, 30 shown in this figure:

A. 14, 18", 28, 32, 34, 36 (all)
B. 14, 28, 34, 36
C. 14, 34, 36
D. 14, 18", 36
E. 32, 34, 36
F. 18", 32, 36
G. 18", 32, 34
H. 14, 18", 34

As represented by the first set (i.e., set "A" above) of example pathways noted above, all six communication pathways 14, 18", 28, 32, 34, 36 depicted in FIG. 3 could be used in a system for delivering pulsed RF energy during a catheter ablation procedure. Alternatively, and as merely one more example, communication pathways 14, 28, 34, and 36 may be the only four communication pathways required in the control system. This is the second example listed above (i.e., set "B"). In each of these communication pathway examples, it is assumed that the generator 20 is always connected to the catheter 12 in some way (as represented in FIG. 3 by the solid line 28 extending between the generator and the catheter). Thus, in yet another example operating scenario, the generator 20 may directly receive temperature feedback from the catheter 12 along, for example, communication pathway 28. The generator 20 could then share that temperature feedback information with the dedicated CPU 30 and/or the pulse control box 22 via one or more of the communication pathways 18", 34, 36. Yet another possible alternative to the system 10" depicted in FIG. 3 would be to switch the locations of the pulse control box 22 and the generator 20, similar to the configuration depicted in FIG. 1, but also include the dedicated CPU 30 depicted in FIG. 3. In this latter optional configuration, there may be a communication pathway (not shown) directly connecting the pulse control box 22 to the catheter 12 (similar to communication pathway 16 in FIG. 1).

Figure 4:
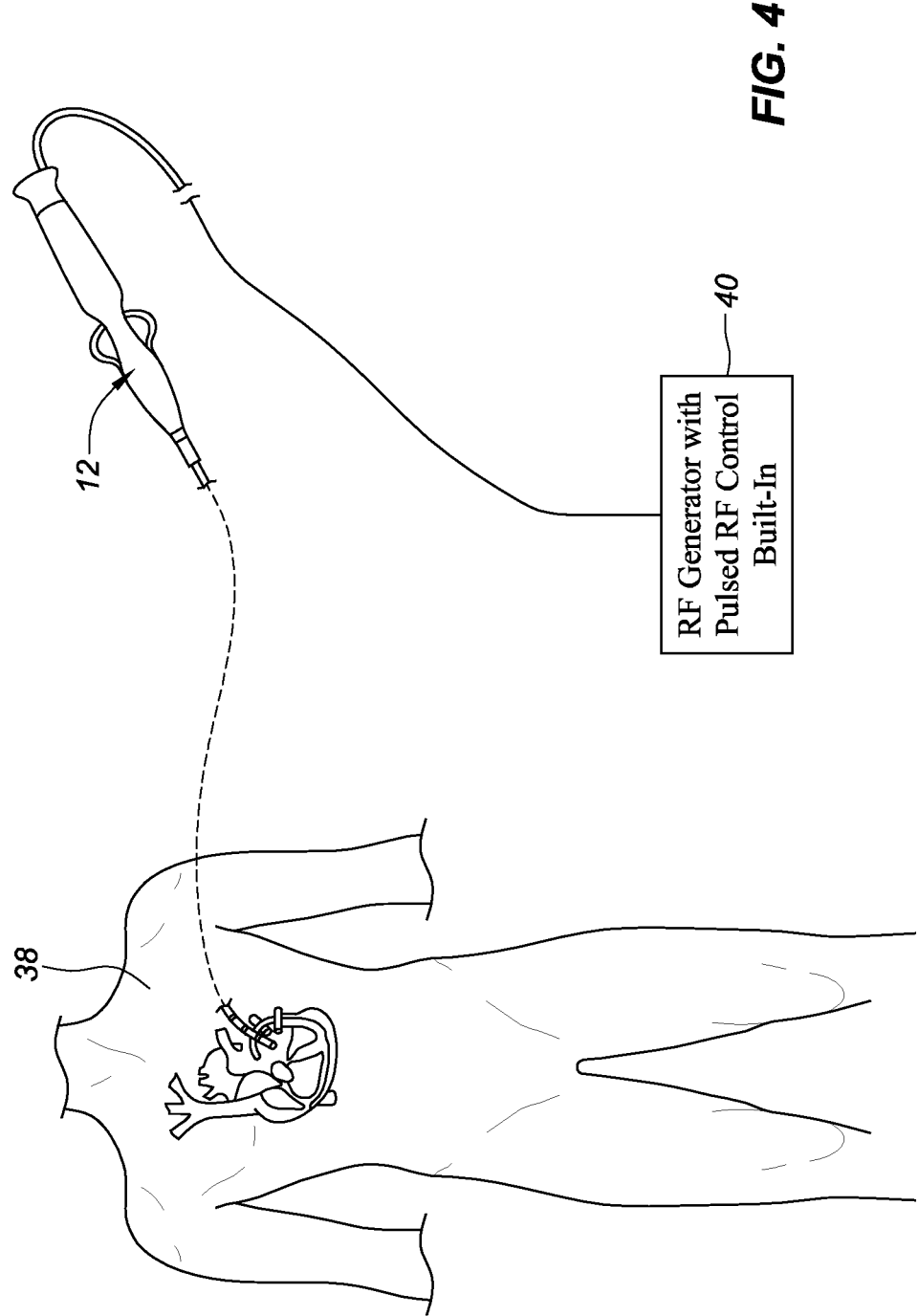
FIG. 4 schematically depicts a catheter in use in a patient and connected to a generator comprising a pulsed RF control system according to the present disclosure.

FIG. 4 schematically depicts a catheter 12 in use in a patient 38 and connected to a generator 40 comprising a pulsed RF control system according to the present disclosure. This figure depicts a portion of a human torso of the patient 38, a heart, a representative catheter tip located in the heart, a representative catheter handle, and the RF generator. As shown in this figure, the catheter is assumed to be connected to the RF generator 40. In this configuration, the pulse control hardware, software, and/or firmware is built into the generator itself.

Figure 5:
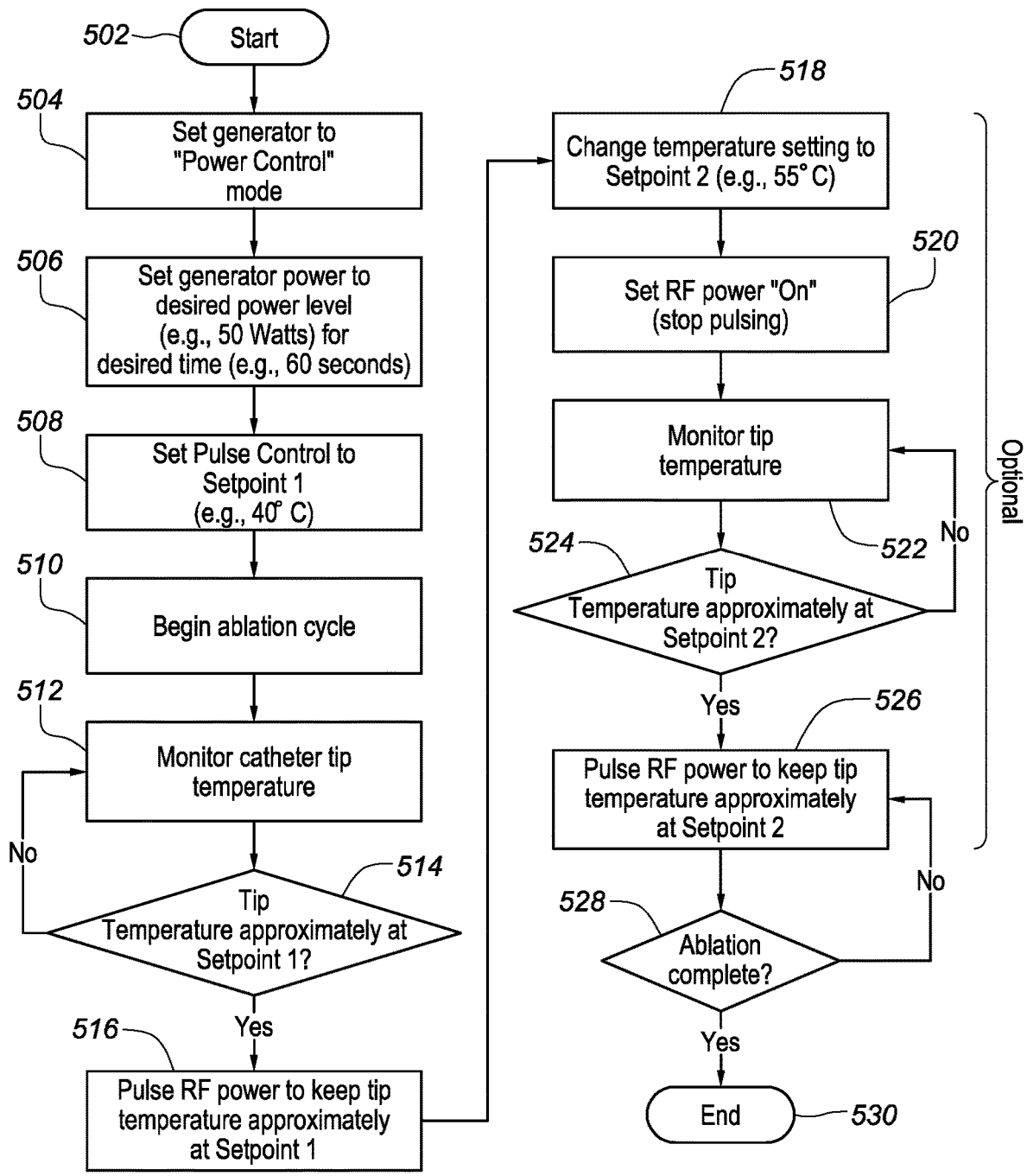
FIG. 5 depicts one possible control flowchart, including various optional steps, for delivering pulsed RF energy to an ablation catheter.

FIG. 5 is a flowchart depicting one possible control flow, including various optional steps, for delivering pulsed RF energy to an ablation catheter. In this representative, and not limiting, example of control flow, the process commences at block 502. At block 504, the generator is placed in a "power-control" mode. Next, at block 506 the generator power is set to a desired power level for a desired initial time. In this representative flowchart, that initial power level is shown as 50 Watts and the initial time is shown as 60 seconds; however, both of these are merely sample values. If, for example, a physician is ablating a portion of the heart that lies near the esophagus, then the physician may choose to use a lower power setting (e.g., 15 Watts) since the physician may desire to create a relatively shallow lesion (e.g., a 1 mm deep lesion). At block 508, the pulse control may be set to set point 1. If, for example, the pulse control box 22 (see, for example, FIG. 1) is a PID controller (also known as a proportional-integral-derivative controller or a three-term controller), set point 1 may relate to the measured process variable (PV). That measured process variable may be the temperature feedback coming from the catheter tip during the ablation cycle. As may be understood by one of skill in the relevant art, a PID controller calculates an error value as the difference between a measured process variable—e.g., measured tip temperature—and a desired set point—e.g., a desired tip temperature. The controller then attempts to minimize the error by adjusting the process through use of a manipulated variable (MV)—e.g., the time that a selected power is actively delivered to an ablation tip. The three parameters in a PID controller are as follows:

1. the proportional value (P)—depends on present error;
2. the integral value (I)—accumulation of past errors; and
3. the derivative value (D)—predictive of future errors based on current rate of change.

In an effort to achieve a gradual convergence to the set point, which, as discussed herein, may be desired catheter tip temperature, the controller calculates a weighted sum of P, I, and D, and then uses that value to adjust the process—here by adjusting the time when RF power is delivered to the ablation tip (e.g., by pulsing the delivery of RF energy to the tip). In one embodiment of the system described herein, a user is allowed to "tune" the three values, namely the P, I, and D values. The controller may be a separate controller as discussed herein and shown in FIGS. 1-3 (e.g., pulse control box 22 in these figures), or may be implemented as a microcontroller or a programmable logic controller (PLC) or in other firmware or software, all of which may be, for example, built directly into the generator 40 as shown in, for example, FIG. 4. In the control systems described herein, RF power is turned "on" and "off" based on the temperature feedback as it is interpreted and analyzed by the pulse control box. In block 510, the ablation cycle begins.

In block 512, the control system monitors the catheter tip temperature. As noted above, this would be the "PV" value in a PID controller. As represented by block 514 and its loop back to block 512, as long as the tip temperature is not close to set point 1, the system continues to permit the delivery of full RF power to the ablation tip and continues to monitor catheter tip temperature at block 512. Once the measured tip temperature is approximately at the value of set point 1 (e.g., 40° C. in one example), the pulse control box (e.g., the PID controller) would begin to pulse the RF energy being delivered to the catheter tip (see block 516) in an effort to keep the tip temperature approximately at set point 1.

Continuing to refer to the flowchart in FIG. 5, at block 518, the temperature setting on the pulse control box 22 is changed to set point 2, which may be, for example, a higher value than set point 1. As shown in FIG. 5, in this example set point 2 is 55° C. At this point in the process, and in order to increase the tip temperature from set point 1 to set point 2, the full RF power may be delivered to the catheter tip (see block 520). In other words, at least initially, the system may stop delivering pulsed RF energy to the ablation tip as the system tries to drive the tip temperature from the set point 1 temperature to the set point 2 temperature. In block 522, the system monitors the tip temperature. In decision block 524, the system compares the temperature at the ablation tip to set point 2. If the tip temperature is not yet approximately equal to the value of set point 2, the system repeatedly returns to block 522 and continues to monitor the tip temperature being reported to the pulse control box. Once the tip temperature is approximately equal to the value of set point 2, control transfers from block 524 to block 526 in FIG. 5.

Block 526 is similar to block 516 and, at this point, the control system begins again to pulse the delivery of RF energy in an effort to keep the tip temperature approximately at set point 2 without overheating the tissue. In decision block 528, the system next attempts to determine whether the ablation is complete (e.g., a physician may stop calling for the delivery of ablation energy). Once it is determined that the ablation is complete (e.g., when, a physician determines that sufficient RF energy has been delivered to the tissue), control transfers to block 530; and all delivery of RF energy to the ablation tip is stopped.

As mentioned, in one of the sample embodiments described herein, the PID controller receives values for set point 1 and set point 2, which may be entered by a user. The PID controller also receives the measured temperature (or multiple measured temperatures if multiple temperature sensors are present) from the catheter tip. The controller then determines when to permit delivery of full power RF energy or pulsed RF energy to the ablation tip, including, in the latter case, the length of the pulses (i.e., the time periods when RF energy is being delivered to the catheter tip) and the length of the time periods when no RF energy is being delivered to the catheter tip. The length of the pulses and the length of the non-pulse time periods may vary continuously. That is, the duration of two adjacent pulses may be different, and the length of two adjacent non-pulse time periods may be different. The PID controller determines algorithmically when to turn the RF power "on" and "off" as it receives real-time (or near-real-time) tip temperature feedback from the ablation catheter.

Figure 6:
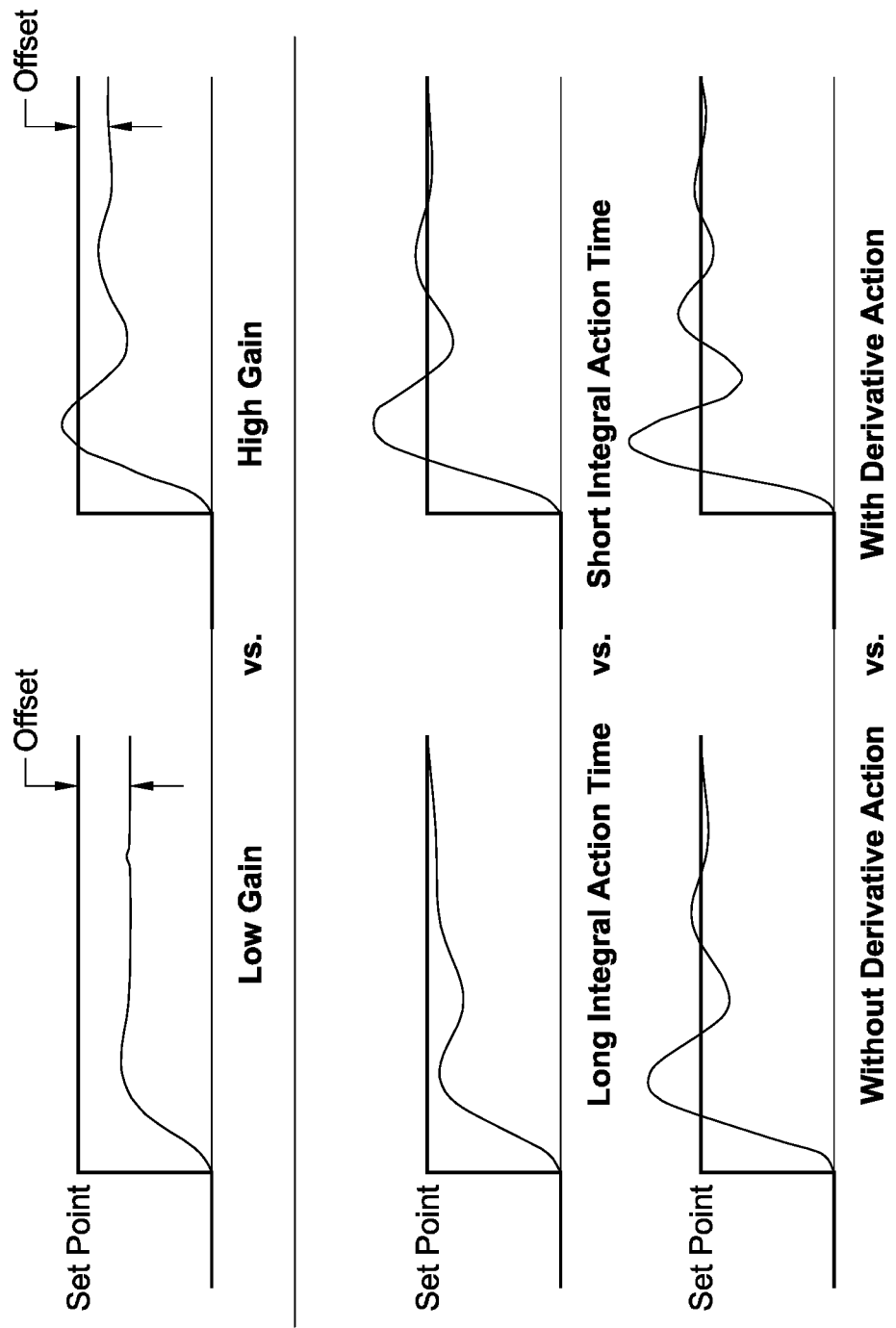
FIG. 6 depicts six representative controller responses, showing how a measured process variable may approach a set point depending on how the controller is configured.

FIG. 6 depicts six representative controller response curves, showing how a measured process variable (which may be the measured tip temperature in the control systems disclosed herein) may approach a set point (which may be the desired tip temperature in the control systems disclosed herein), depending on how the controller is configured. In the ablation controllers discussed herein, the controller response curve labeled "Long Integral Action Time" in FIG. 6 may be a desirable controller response as the tip temperature is driven from its starting temperature to the desired ablation temperature. In particular, in this curve, which is located in the middle of the left three curves in FIG. 6, the temperature would never exceed the set point temperature (e.g., set point 1 or set point 2 in FIG. 5), but would reach the set point temperature in a timely and efficient manner.

Figure 7:
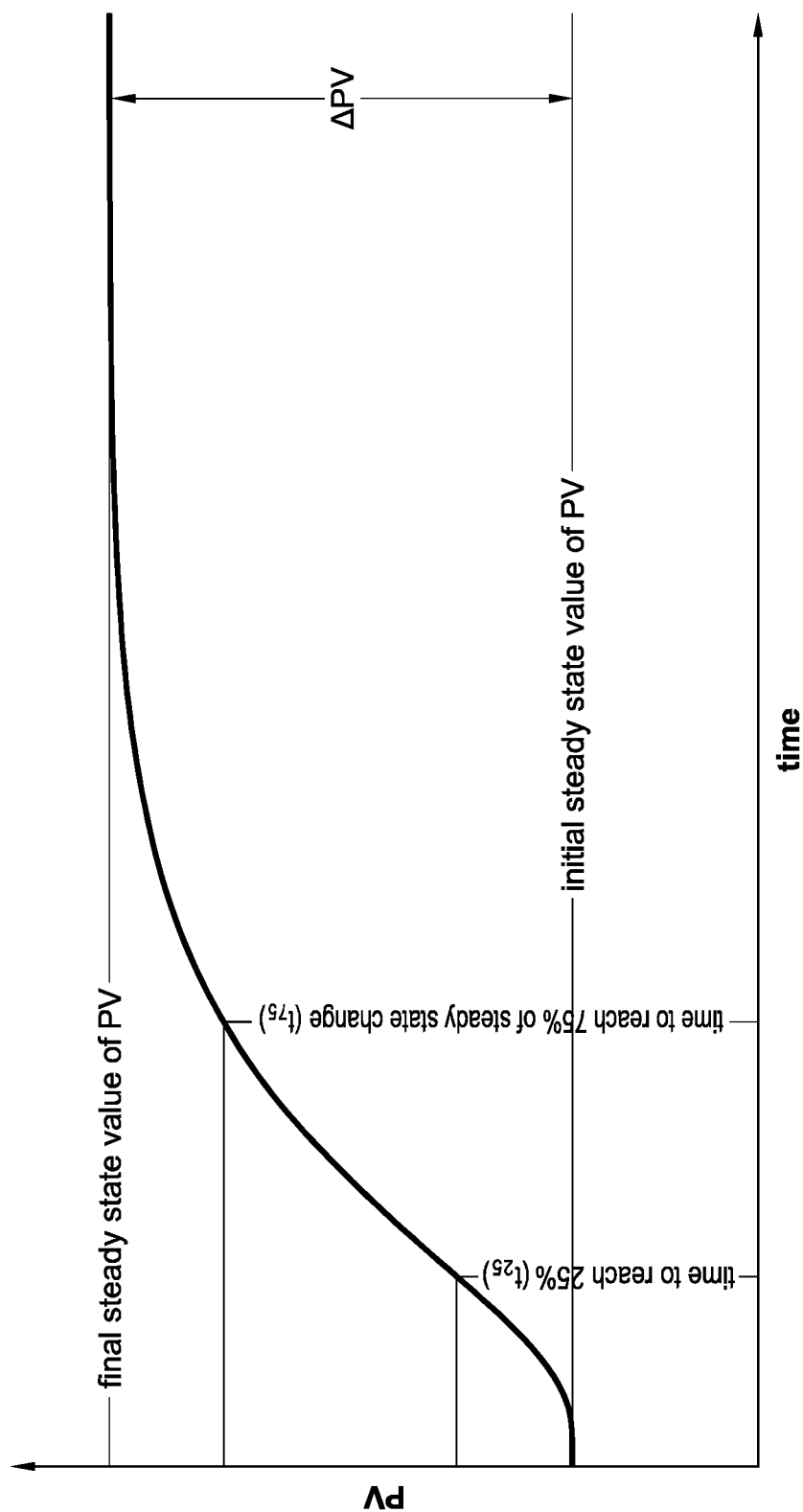
FIG. 7 depicts a representative controller response and depicts how a measured process variable (PV) at a first set point ("initial steady state value of PV") may be driven to a second set point ("final steady state value of PV").

FIG. 7 depicts a representative controller response curve and depicts how a measured process variable (PV) at a first set point ("initial steady state value of PV") may be driven to a second set point ("final steady state value of PV"). This 'dual set point' configuration is represented in the full flowchart of FIG. 5, which is described above. It should be noted, however, that such a dual set point control scheme is not required. In other words, an effective controller could drive the catheter tip temperature directly to the set point ultimately desired, without driving to a first value (e.g., set point 1) and then driving to a second value (e.g., set point 2). Hence, blocks 518-526 are labeled "optional" in FIG. 5. If these five blocks were not present, the "No" decision line from block 528 would go to block 516. The control system would then be configured to drive to a single set point. That said, there are potential advantages to keeping all blocks of the control scheme depicted in FIG. 5. For instance, the control system of FIG. 5 may have some distinct safety advantages. For example, set point 1 could be an initial temperature that is somewhere between the starting temperature of the ablation tip and the ultimate desired temperature for the ablation tip. If the system is able to reach the set point 1 value effectively and while remaining under control, that would provide the user with confidence that the tip is in contact with the tissue and that the controller is working properly before the tip temperature reaches a potentially dangerously-high temperature. Once set point 1 is reached (i.e., where control transitions from block 514 to block 516 in FIG. 5), the user will have confidence that the controller is functioning properly and could then, at block 518 of FIG. 5, input a higher (ultimately desired) working temperature for creating lesions.

To enable the ablation temperature control system described above to work most effectively, it may be desirable to have an ablation tip having a relatively low thermal mass (also known as ablation tip having high thermal sensitivity). If the ablation tip has a relatively low thermal mass, it more rapidly heats (i.e., it comes to temperature quickly) and cools (i.e., it does not remain hot for long after power is removed), enabling tighter control of the tip temperature and less "coasting" of the tip temperature past a desired set point as well as more rapid reduction in tip temperature when RF power is removed from the tip. In fact, such a tip may cool down at the same rate as the tissue, which would inform the user whether the tip became dislodged during ablation. Remaining FIGS. 8-25, which are described further below, depict various embodiments and components of ablation catheter tips that can be used effectively with the pulsed RF control systems described herein. The catheter tips disclosed herein are not necessarily the only tips that could be used with the pulsed RF control systems described herein.

FIG. 8 is a fragmentary, isometric view of various components comprising an embodiment of a tip 42 at the distal end of an ablation catheter that could be used with the pulsed RF control systems disclosed herein. In this embodiment, a conductive shell 44 (e.g., a platinum shell, a platinum iridium shell, or a gold shell) with irrigation ports or holes is present at the most distal end of the catheter components shown in FIG. 8. The conductive shell 44 (which may weigh, for example, 0.027 g) includes a shell distal end portion 48 and a shell proximal end portion 50, which may comprise one or more parts or components. In this particular embodiment, the shell 44 includes six irrigation holes 46, two of which are visible in this isometric view. Also visible in FIG. 8 is an optional shank 52 comprising an annular or washer-shaped brim 54 and a cylindrical open crown 56, which together define the top-hat-shaped shank. In this embodiment, the conductive shell 44 and the shank 52 effectively encase an ablation tip insert 58 (see, for example, FIG. 10), the proximal surface 60 of which is partially visible in FIG. 8. An electrical lead wire 62 is shown connected (e.g., by soldering or welding) to the shank 52. Alternatively, the electrical lead wire 62 may be directly connected to the conductive shell 44. A number of lead wire pairs 64 for the temperature sensors comprising part of the tip may be seen extending rearwardly or proximally in FIG. 8. Finally, FIG. 8 also shows two components of an irrigation tube assembly 66 extending proximally in FIG. 8 (i.e., rightwardly in this figure). Although the conductive shell 44 depicted in the figures includes six irrigation holes 46, more or fewer holes may be used, and the size of the holes may be larger, or smaller, or a mix of larger and smaller holes.

Using the control systems described herein, it may be completely unnecessary to irrigate the ablation tip. FIG. 9 is similar to FIG. 8, but the conductive shell 44' depicted in FIG. 9 does not include any irrigation ports or holes through it (compare element 46 in FIG. 8). Thus, this is a non-irrigated catheter tip 42' that could be used in combination with the pulsed RF control systems described herein. Most of the discussion below focuses on the irrigated catheter tip embodiment 42 of FIG. 8, but much of what is said below regarding the embodiment 42 depicted in FIG. 8 applies equally well to the non-irrigated catheter tip embodiment 42' depicted in FIG. 9, with the exception of the discussion of the irrigation features. It should also be noted that, although the irrigation tube assembly 66 (shown in FIG. 8) is not necessary in the non-irrigated catheter tip embodiment 42' depicted in FIG. 9 (and, thus, is not shown in FIG. 9), the irrigation tube assembly 66 could be present on the non-irrigated catheter tip embodiment. Further, as also shown in FIG. 9, the proximal surface 60 of the ablation tip insert of the non-irrigated embodiment 42' may be slightly different from the proximal surface 60 (FIG. 8) of the ablation tip insert 58 (see also FIG. 10) of the irrigated embodiment 42 (FIG. 8). In particular, the proximal surface 60 may not include the main channel 84, which is discussed further below in connection with FIG. 10. The non-irrigated embodiment of FIG. 9 could, however, just as easily use the same ablation tip insert 58 and the irrigation tube assembly 66 shown in the irrigated catheter tip embodiment 42 of FIG. 8, which would make it possible, for example, to manufacture both irrigated and non-irrigated embodiments on a single assembly line, and would likely result in the two embodiments exhibiting more similar structural integrity during use.

Figure 10:
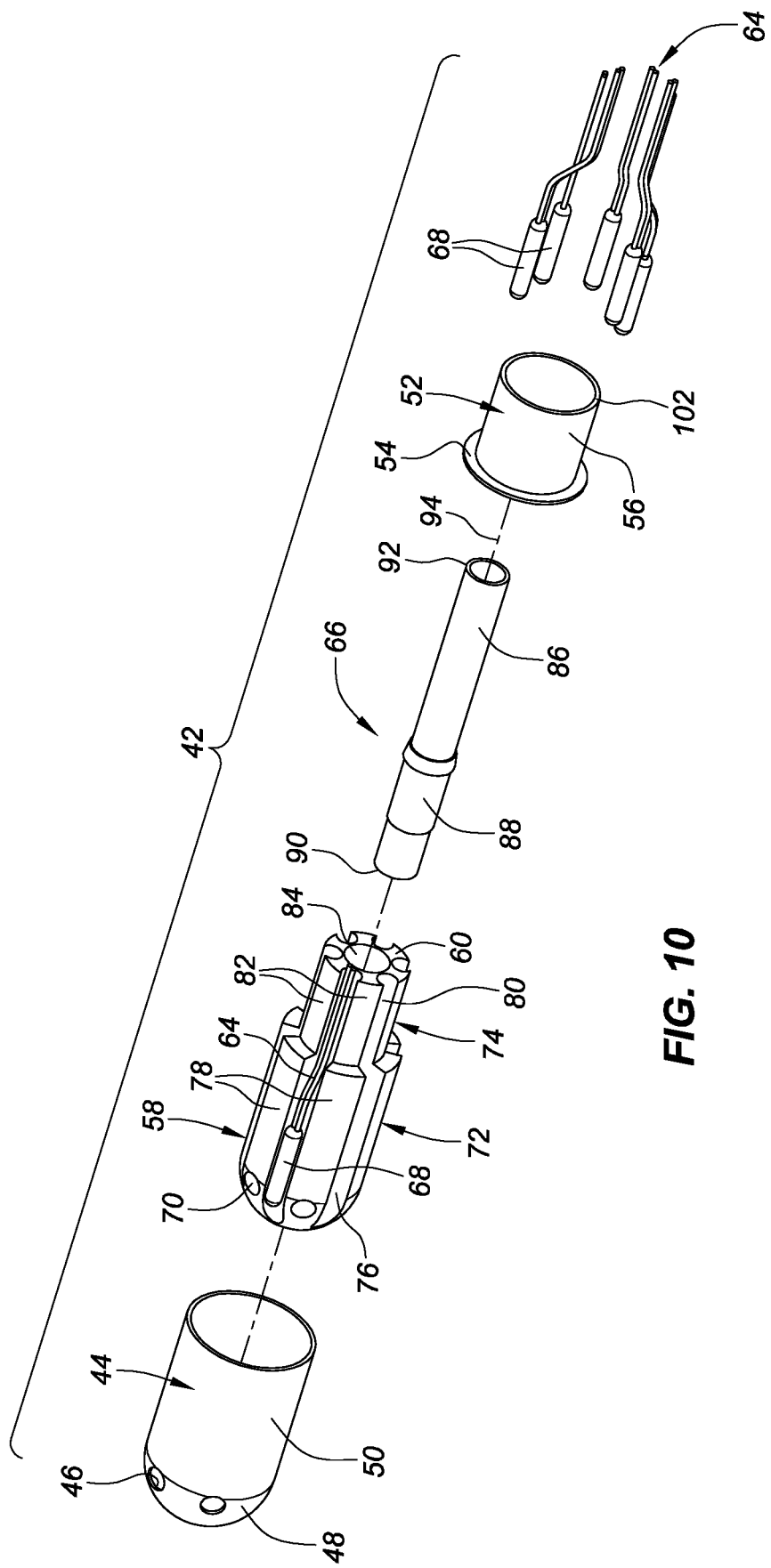
FIG. 10 is an exploded, isometric view of the catheter tip depicted in FIG. 8, showing additional components and features.

FIG. 10, which is an exploded, isometric view of the catheter tip 42 depicted in FIG. 8, is described next, starting with the elements shown in the upper left-hand portion of that figure and working toward the lower right-hand portion of the figure. FIG. 10 again depicts the conductive shell 44, but this time exploded away from the other components of the tip shown in FIGS. 8 and 9 thereby revealing additional features and components. To the right of the conductive shell in FIG. 10 is an assembly of an ablation tip insert 58 and one temperature sensor 68 (e.g., a thermocouple). As may be seen in FIG. 10, the tip insert 58 includes a plurality of lateral irrigation channels 70 that are sized and arranged to align with complementary irrigation holes 46 through the conductive shell 44. To facilitate assembly, the diameter of the lateral irrigation channels 70 in the tip insert 58 may be smaller than the complementary holes 46 through the conductive shell 44. Thus, it would be less critical to precisely align the lateral irrigation channels with the holes through the conductive shell during manufacturing, and the exiting irrigant would have less of an opportunity to contact the conductive shell before reaching a blood pool.

The tip insert, which may be a unitary piece, includes a main body 72 and a stem 74. The tip insert 58 can be constructed from, for example, plastic (such as PEEK, which is polyether ether ketone) or thermally-insulative ceramic. In the depicted embodiment, the main body portion 72 includes a plurality of optional, longitudinally-extending sensor channels or ditches 76. In FIG. 10, a thermal sensor 68 is shown mounted in one of these ditches 76. Each of the sensor ditches is separated from the next adjacent sensor ditch by a longitudinally-extending shell seat 78. The plurality of shell seats between the sensor ditches are configured to ride against, or very near to, the inner surface of the conductive shell 44. Similarly, the stem 74 of the tip insert 58 defines a plurality of longitudinally-extending wire channels or ditches 80 separated by a plurality of longitudinally-extending shank seats 82. The ditches 76, 80 are configured to carry temperature sensor lead wires on their path to the proximal end of the catheter. The shank seats 82 are sized and configured to ride against, or very near to, the inner surface of the cylindrical open crown portion 56 of the shank 52. The tip insert 58 includes a main channel 84 having a circular cross-section that, as shown in the figures and as described further below, may include more than one inner diameter.

Downward to the right of the tip insert 58 in FIG. 10 is an irrigation tube assembly 66. The irrigation tube assembly comprises, in this embodiment, a central irrigation tube 86 and an optional seating sleeve 88. The central irrigation tube 86 has a distal end 90 and a proximal end 92 and may be constructed from a polymer, such as polyimide. This central irrigation tube may extend proximally toward a catheter handle, or may extend proximally all the way to the catheter handle. The optional seating sleeve 88, as shown in the embodiment depicted in FIG. 10, may include a cylindrical portion and a frustoconical boss. The seating sleeve may be positioned at a desired longitudinal location along the outer surface of the central irrigation tube 86 and then may be fixed in place (for example, by an adhesive or sonic welding or via some other technique). The irrigation tube assembly would then be mounted in the tip insert by, for example, adhesive. If the optional seating sleeve is not included (e.g., to simplify tip construction and manufacturing), the central irrigation tube 86 could be adhered directly to the tip insert 58. To the right of the irrigation tube assembly in FIG. 10 is the optional shank 52. Details of the shank are described further below in connection with, for example, FIG. 14. To the right of the shank are five additional temperature sensors 68. In particular, in this particular embodiment of the tip, six temperature sensors are radially disposed symmetrically about the catheter longitudinal axis 94 (see, for example, FIG. 8). Since one of those six thermal sensors is depicted already in position on the tip insert 58 in FIG. 10, the remaining five temperature sensors are shown in the lower right-hand portion of FIG. 10, oriented and arranged so as to slip into the remaining five complementary sensor ditches 76 formed in the tip insert.

Figure 11:
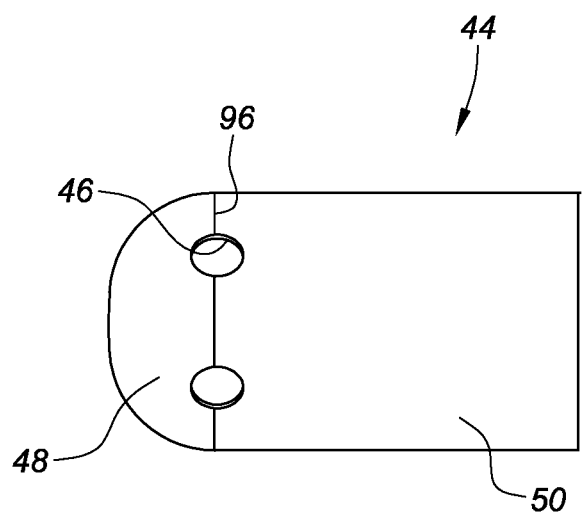
FIG. 11 is a side view of the conductive shell depicted in, for example, FIGS. 8 and 10.
Figure 12:
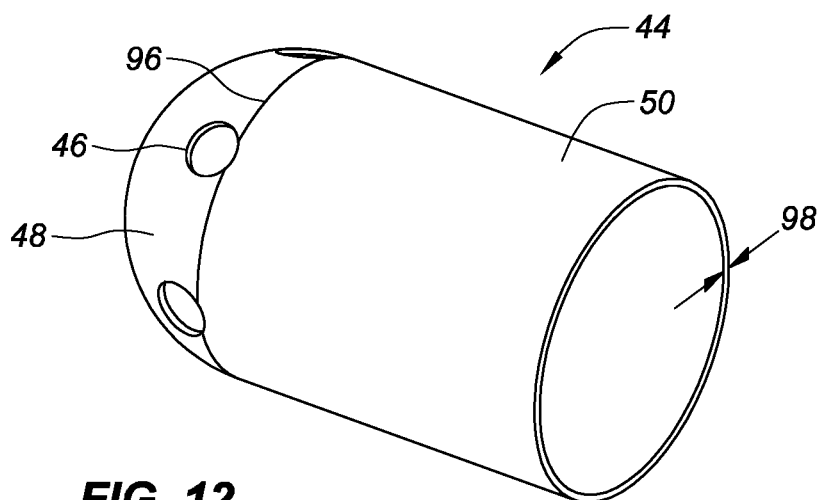
FIG. 12 is an isometric view of the conductive shell depicted, for example, in FIGS. 10 and 11.
Figure 13:
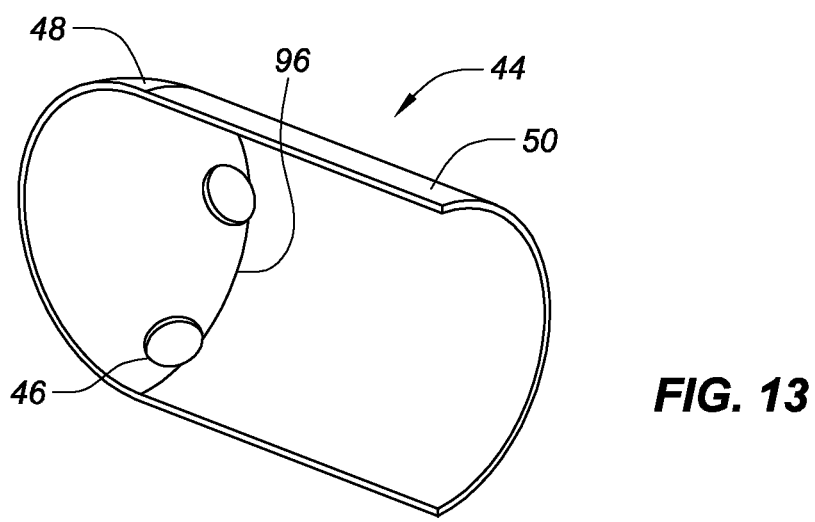
FIG. 13 is a cross-sectional view showing the interior of the conductive shell depicted in, for example, FIGS. 10-12.

FIGS. 11-13 are additional views of the conductive shell 44 depicted in, for example, FIGS. 8 and 10. As shown in these figures, the conductive shell may comprise a hemispherical or nearly-hemispherical domed distal end 48 and a cylindrical body 50. In the figures, a 'seam' 96 is shown between the domed distal end 48 and the cylindrical body 50. This may be merely a circumferential transition line between the cylindrical body and the domed distal end of a unitary component; or, alternatively, it may be the location where the cylindrical body is connected to the domed distal end by, for example, welding. In one embodiment, the wall thickness 98 of the shell is 0.002 inches, but alternative wall thicknesses also work. The conductive shell could be formed or manufactured by, for example, forging, machining, drawing, spinning, or coining. Also, the conductive shell could be constructed from molded ceramic that has, for example, sputtered platinum on its external surface. In another alternative embodiment, the conductive shell could be constructed from conductive ceramic material.

Figure 14:
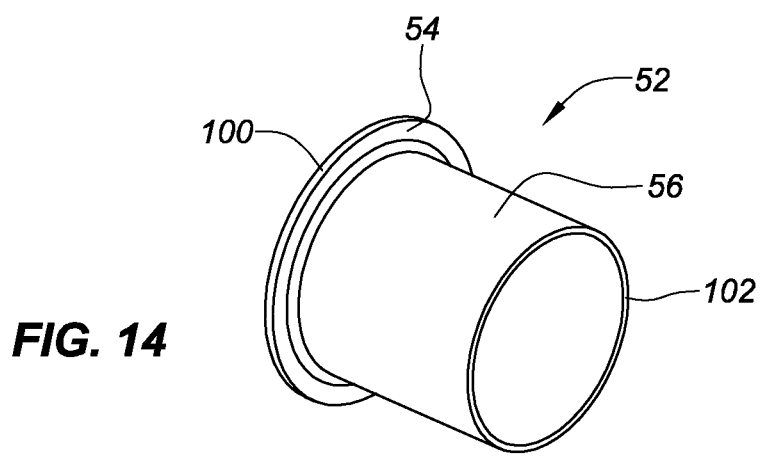
FIG. 14 is an enlarged isometric view of the shank also depicted in, for example, FIGS. 8-10.

FIG. 14 is an enlarged, isometric view of the shank 52 also depicted in, for example, FIGS. 8-10. The brim 54 may include a circumferential outward edge 100 that, as described below, may be connected by welding or soldering to a surface (e.g., the inner surface) of the cylindrical body 50 of the conductive shell. The shank includes a cylindrical open crown 56 that also defines an inner surface. As described above, the inner surface of the cylindrical open crown is sized and configured to slide over the shank seats 82 defined on the stem of the tip insert 58. The cylindrical open crown of the shank also defines a proximal end or edge 102.

Figure 15:
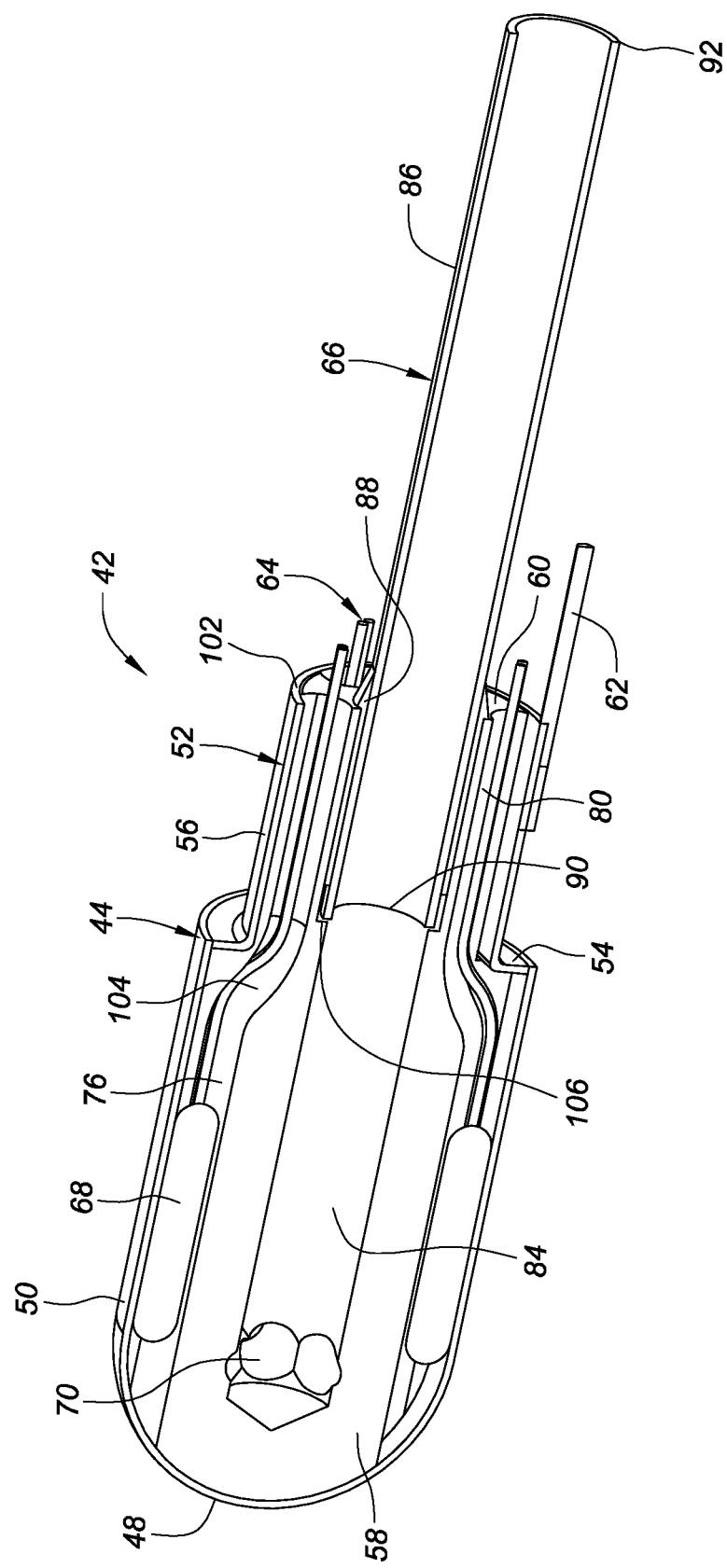
FIG. 15 is an isometric, cross-sectional view of the various catheter tip components also depicted in FIG. 8.

FIG. 15 is an isometric, cross-sectional view of various components of the catheter tip 42 also depicted in FIG. 8 and clearly shows two temperature sensors 68 mounted in their respective temperature sensor ditches 76. As may be clearly seen in this figure, the sensor ditches may include a wire ramp 104 that allows the thermal sensor lead wires 64 to transition from the sensor ditches 76 (formed in the main body of the tip insert) to the wire ditches 80 (formed in the stem of the tip insert). In this configuration, the circumferential outer edge 100 (as shown in FIG. 14) of the brim 54 of the shank 52 is shown riding against the inner surface of the cylindrical body of the conductive shell 50. The shank may be welded or soldered to the conductive shell at this interface to ensure good electrical contact between the shank and the shell. In particular, since the tip electrode lead wire 62 may be electrically connected to the cylindrical open crown 56 of the shank 52 in this embodiment, the shank must be conductively connected to the conductive shell 44 in a manner that permits transfer of energy from the tip electrode lead wire 62 to the shank 52 and then to the conductive shell 44.

Looking more closely at the irrigation tube assembly 66 shown in FIG. 15, it is possible to see that the distal end 90 of the central irrigation tube 86 rides against an inner annular ledge 106 formed as part of the tip insert 58. Further, the frustoconical boss defines a distally-facing ledge or lip that rides against the distal end of the stem 74 of the tip insert 58. Thus, the irrigation tube assembly seats against both the proximal surface 60 of the tip insert 58 as well as the inner annular ledge 106 defined along the longitudinal irrigation channel 84 extending through most of the tip insert 58. It should be noted that when the temperature sensors are in place in the tip insert, when the irrigation tube assembly is mounted in the tip insert, and when the conductive shell and the shank are in position, any voids in the assembled tip (other than the lateral irrigation channels 70) may be filled with potting material, providing a durable assembled set of components. It should also be noted that the outer surface of the temperature sensors are mounted so as to at least be in close proximity to, and preferably so as to be in physical contact with, the inner surface of the conductive shell 44. As used herein, "in close proximity to" means, for example, within 0.0002 to 0.0010 inches, particularly if a conductive adhesive or other bonding technique is used to bond the temperature sensors to the inner surface of the shell. Depending on the specific properties of the sensors, the construction and materials used for the shell, and the type of conductive adhesive or the other bonding technique employed, it is possible that enough temperature sensitivity may be achieved despite even larger gaps between the sensors and the conductive shell, as long as the sensors are able to readily sense the temperature of the tissue that will be touching the outer surface of the conductive shell during use of the catheter tip. Also, the distal end portions of the sensor ditches 76 may be shallower than the proximal end portions of the sensor ditches. In this manner, when a temperature sensor 68 is mounted in its respective sensor ditch, the distal most portion of the temperature sensor is "lifted" toward and possibly against the inner surface of the cylindrical body of the conductive shell 44. This helps to establish good thermal conductivity between the conductive shell and the thermal sensor or sensors mounted inside of the shell.

Figure 16:
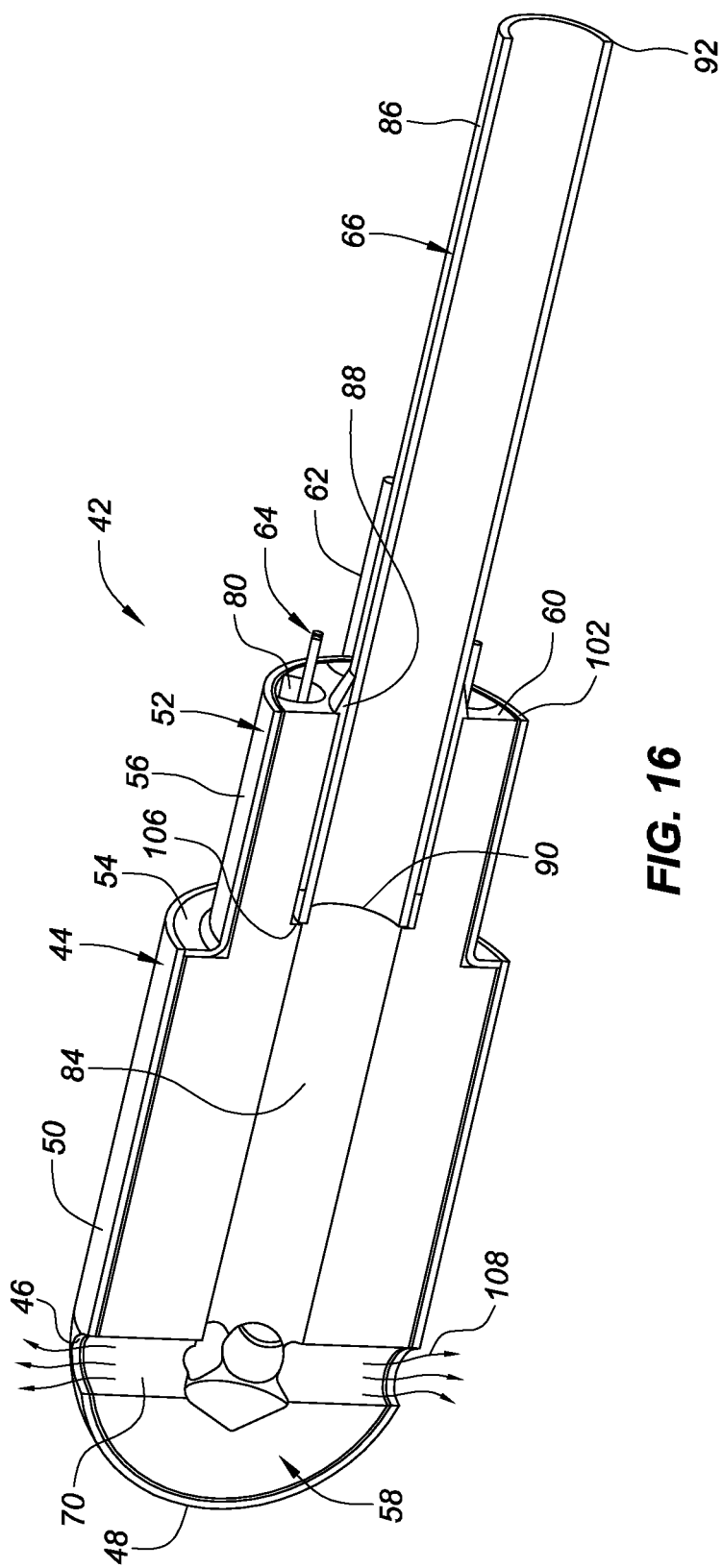
FIG. 16 is similar to FIG. 15, but is a cross-sectional view taken at an angular orientation that bisects two of the lateral irrigation channels.
Figure 18:
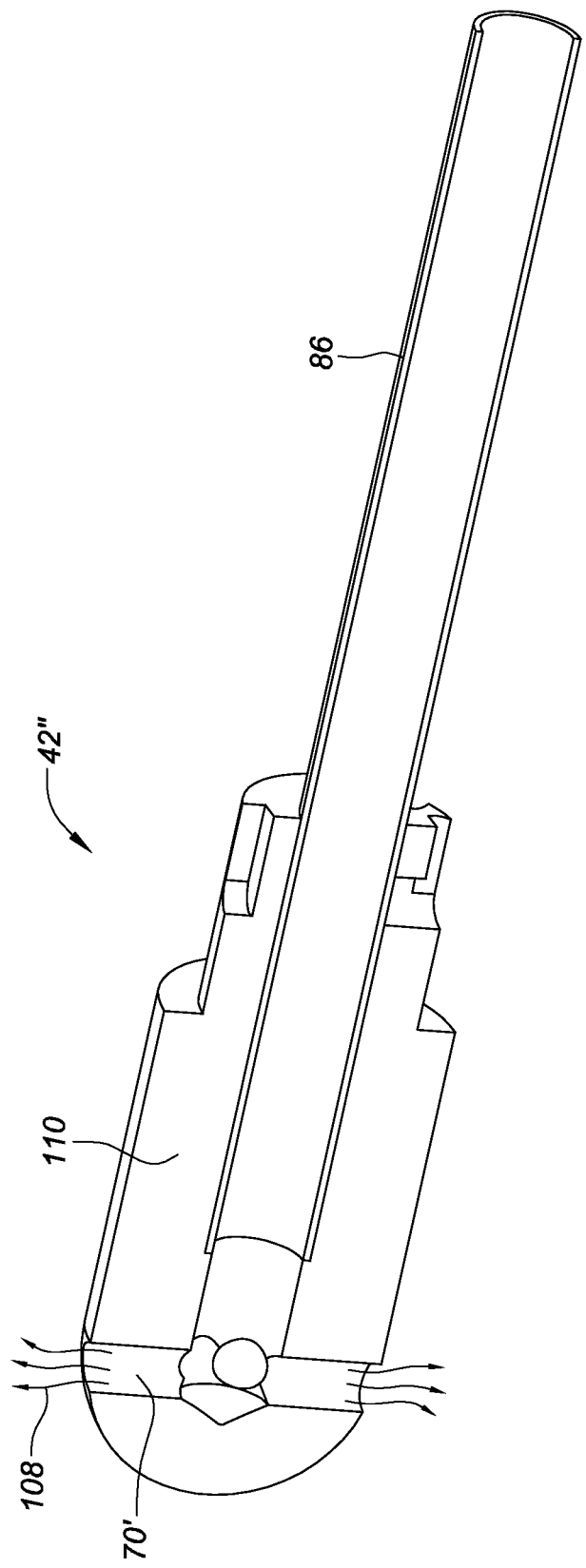
FIG. 18 is a fragmentary, isometric, cross-sectional view of a prior art, solid platinum (or solid platinum iridium) irrigated catheter tip with a polymer irrigation tube mounted in its proximal end.

FIG. 16 is similar to FIG. 15, but is a cross-sectional view taken at a slightly different angular orientation from that shown in FIG. 15, to thereby reveal two of the lateral irrigation channels 70 configured to deliver irrigant 108 outside of the tip 42. Since the conductive shell is very thin in these embodiments, and since the tip insert is constructed from an insulative material, the irrigant, when used, has very little ability or opportunity to influence the temperature of the conductive shell 44. As shown to good advantage in FIG. 16, the irrigant exiting the lateral irrigation channels touches the inner edges of the holes 46 through the conductive shell before exiting to the surrounding blood. This may be contrasted to what is shown in FIG. 18, which depicts a prior art catheter tip 42". In particular, FIG. 18 depicts a solid platinum (or platinum iridium) tip 110 with a polymer irrigation tube 86 mounted in it. In this solid platinum tip (which may weigh, for example, 0.333 g), the irrigant 108 flows through and directly contacts a portion of the platinum tip before reaching the lateral irrigation channels 70' and then exiting the tip. Thus, there is a relatively extended period of time where the cool irrigant rides directly against the platinum comprising the conductive tip. Thus, in the embodiment depicted in FIG. 18, the irrigant has a much greater opportunity to influence the temperature of the tip than does the irrigant in the embodiment depicted in, for example, FIG. 16.

Also, during ablation with a solid platinum tip 110, essentially the entire tip must heat up before a sensor embedded in the tip senses a temperature rise. Thus, not only does the portion of the tip in contact with the tissue being treated heat up, but also the entire tip gets hot, even portions of the tip that are remote from the tissue being treated. Blood flow around the entire solid platinum tip robs heat from the tip, which further distorts the temperature sensed by a sensor embedded in the solid platinum tip; and temperature averaging issues may come into play. For at least these reasons, the temperature sensor embedded in a solid platinum tip is less capable of accurately reporting the temperature in the immediate vicinity of the tissue being treated. In contrast, in embodiments such as the one depicted in FIGS. 15 and 16, with a relatively thin conductive shell 44 surrounding an insulative tip insert 58, the temperature of the conductive shell in the immediate vicinity of the tissue-tip interface heats up quickly, and the sensor 68 closest to that portion of the conductive shell rapidly senses and reports a temperature rise in the immediate vicinity of the tissue-tip interface. It is not necessary for the entire tip to heat up before the sensor can report a temperature rise in the tissue, the blood flowing around the entire tip thus has less of an opportunity to distort the sensed tip temperature, and fewer temperature averaging issues come into play.

Figure 17:
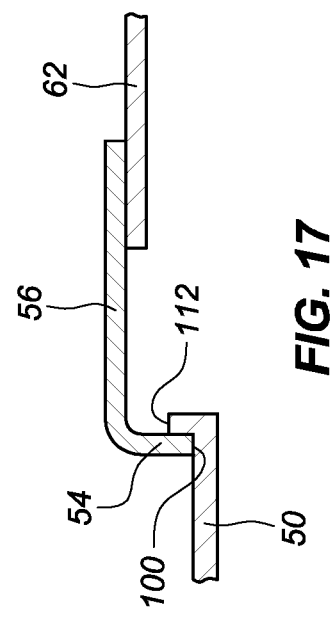
FIG. 17 is an enlarged, fragmentary, cross-sectional view showing a possible interconnection between the shell cylindrical body, the shank, and an RF lead wire.

FIG. 17 is an enlarged, fragmentary, cross-sectional view showing one possible interconnection between the cylindrical body 50 of the conductive shell 44, the shank 52, and the RF lead wire 62. As shown in this figure, a proximal edge 112 of the cylindrical body 50 of the conductive shell is bent around the circumferential outward edge 100 of the shank brim 54. The shank brim and the shell body are then connected by welding or soldering, for example. Thus, energy coming from the RF lead wire 62 can be delivered to the shank crown 56, conducted to the shank brim 54, and then delivered to the cylindrical body 50 of the conductive shell.

Figure 19:
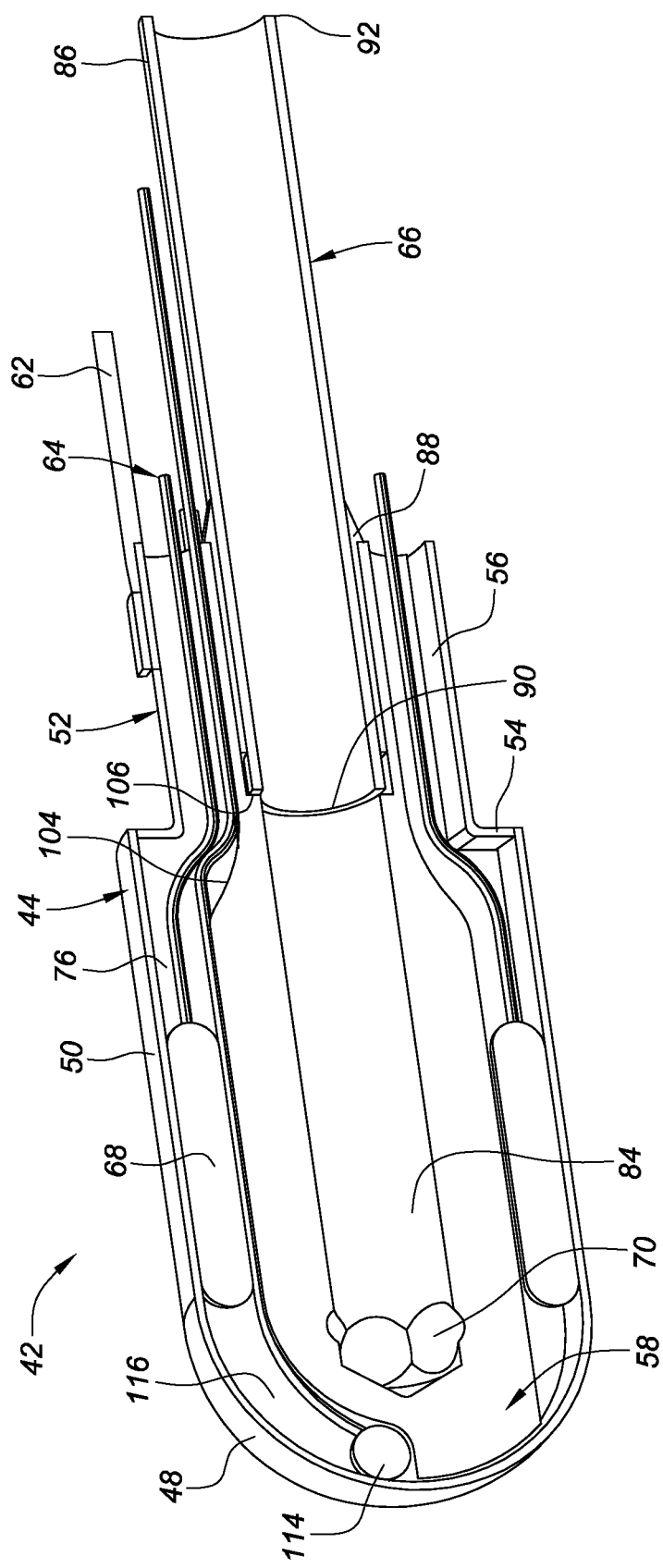
FIG. 19 is similar to FIGS. 15 and 16, and depicts another fragmentary, isometric, cross-sectional view, but this time taken from an angular orientation that clearly shows a distal-most thermal sensor.

FIG. 19 is similar to FIGS. 15 and 16, and depicts another fragmentary, isometric, cross-sectional view, but this time taken from an angular orientation that clearly shows a distal-most thermal sensor 114. In particular, this figure clearly depicts an arc-shaped channel extension 116 extending from one of the sensor ditches 76. As shown in this embodiment, the distal-most thermal sensor (i.e., a seventh thermal sensor in this embodiment) can thus be placed very near to the most distal portion of the tip 42. This distal-most thermal sensor is shown having a spherical shape in FIG. 19 and being placed ahead of (i.e., distally of) one of the radially-disposed thermal sensors 68.

Figure 20:
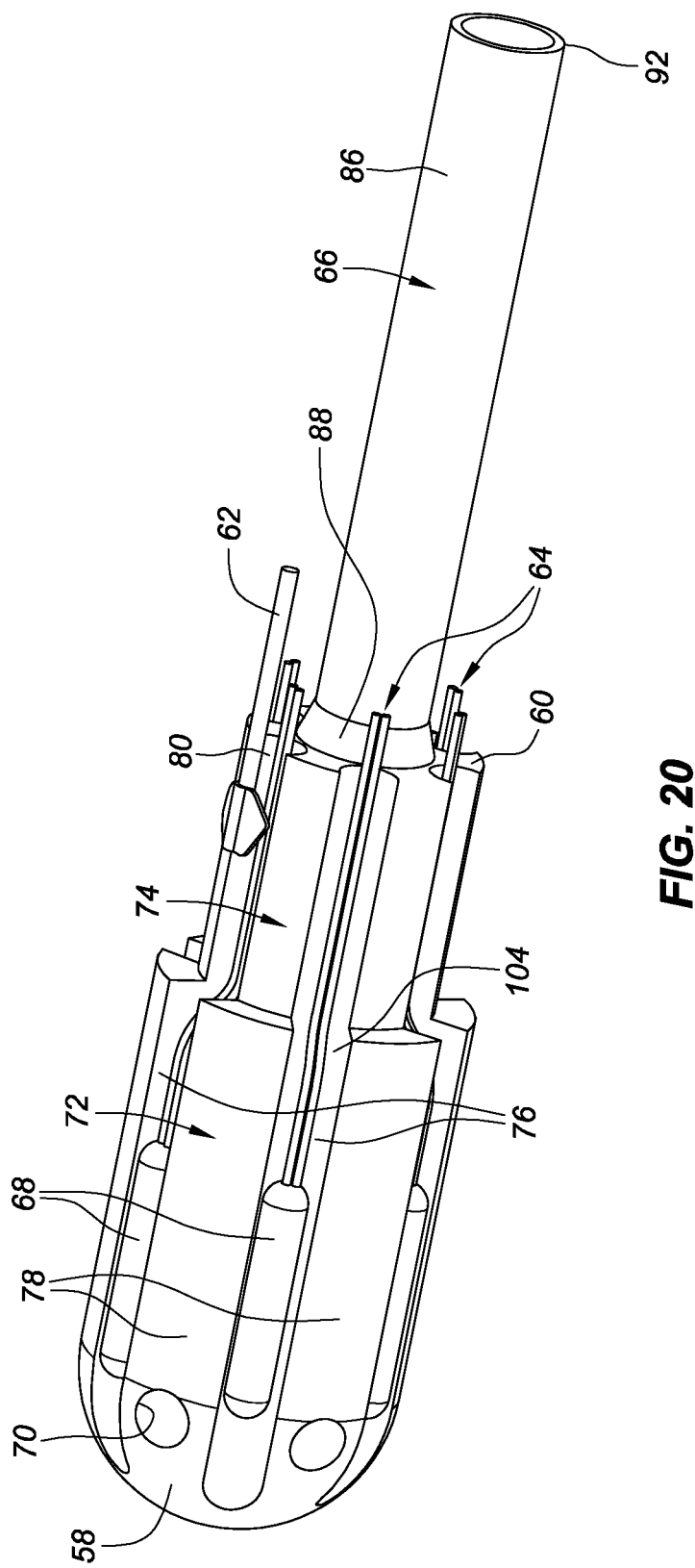
FIG. 20 is an isometric view of components of the tip also depicted in, for example, FIGS. 8, 10, 15, 16, and 19.

FIG. 20 is an isometric view of components of the tip also depicted in, for example, FIGS. 8, 10, 15, 16, and 19. In this figure, all six of the radially-disposed thermal sensors 68 are in place in their respective sensor ditches 76. The seventh, distal-most thermal sensor may also be in place, but is not shown in this particular figure. This figure also clearly shows the frustoconical boss comprising part of the optional seating sleeve 88 with its distally-facing surface or tip resting against the proximally-facing surface 60 of the tip insert 58.

Figure 21:
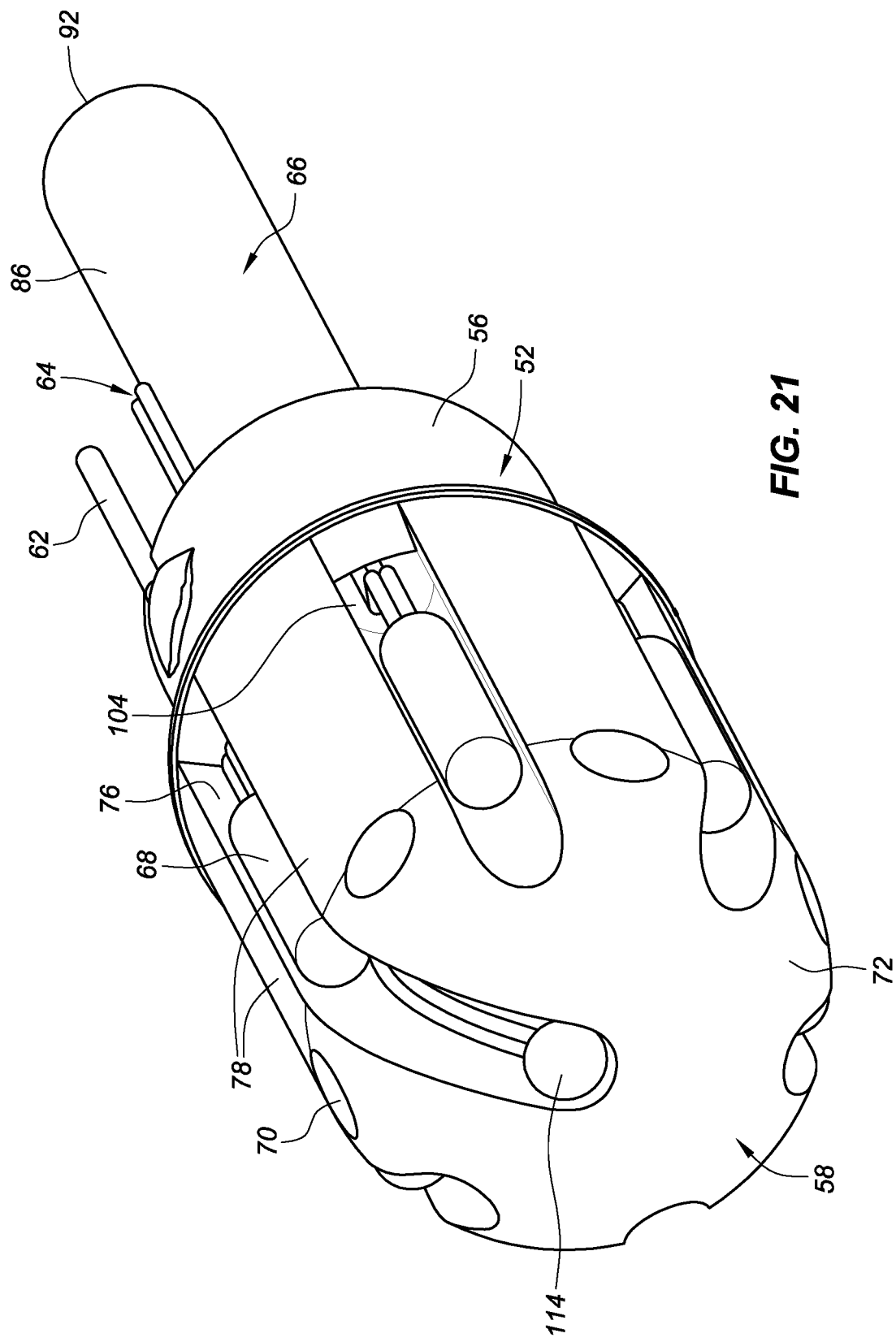
FIG. 21 is similar to FIG. 20, but shows the catheter tip components in a different orientation, revealing the distal-most thermal sensor; and this view also includes the shank, which is not present in FIG. 20.

FIG. 21 is similar to FIG. 20, but shows components of the catheter tip from a different view, wherein the distal-most thermal sensor 114 (i.e., the seventh thermal sensor in this embodiment) is visible, and this view also includes the shank 52, which is not present in FIG. 20. In FIG. 21, the shank is in place over the stem of the tip insert, which helps clarify the benefit of the wire ramps 104 connecting the sensor ditches 76 to the wire ditches, both of which are formed in the tip insert.

Figure 22:
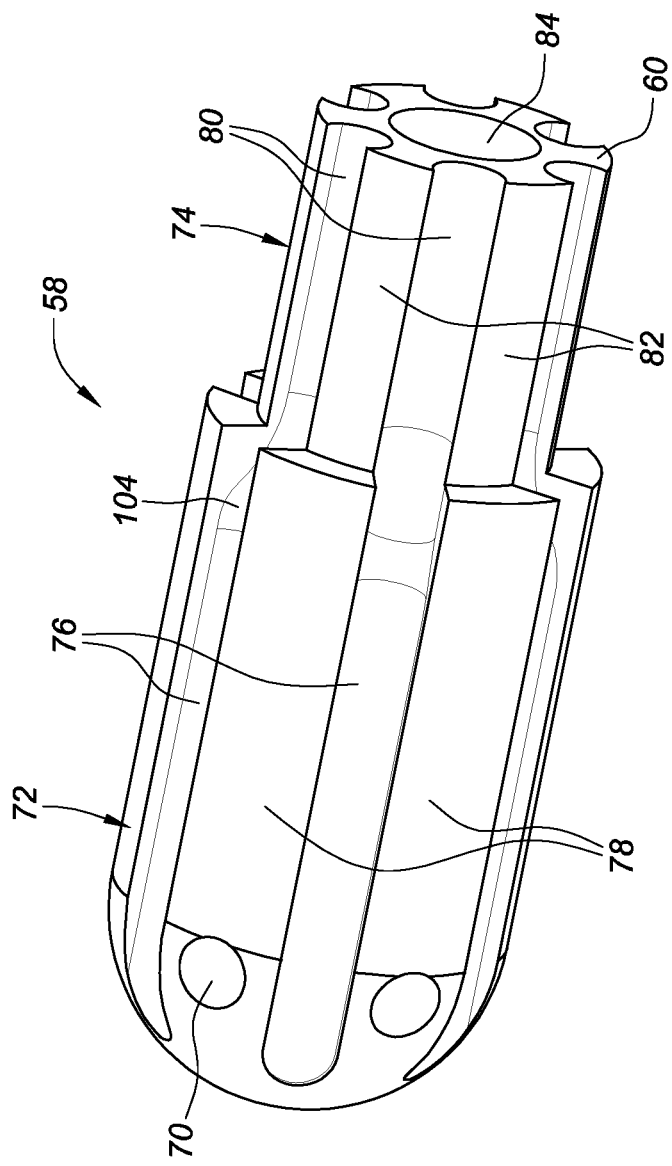
FIG. 22 is an isometric view of the thermally-insulative ablation tip insert also depicted in FIG. 21.

FIG. 22 is an isometric view of just the thermally-insulative ablation tip insert 58 also depicted in FIG. 21, but without any other tip components. All of the ablation tip inserts described herein are preferably constructed from thermally-insulative material. They could be constructed from, for example, ULTEM, plastic (such as PEEK, which is polyether ether ketone) or thermally-insulative ceramic. In this particular embodiment, the tip insert includes six laterally-extending irrigation channels 70, each of which has a longitudinal axis arranged substantially perpendicular to the longitudinal axis of the tube channel that is itself arranged substantially parallel to the catheter longitudinal axis 94. The laterally-extending irrigation channels connect a distal end of the tube channel 84 to an outer surface of the tip insert. It should be noted that the laterally-extending irrigation channels could be arranged at a different angle (i.e., different from 90°) relative to the tube channel longitudinal axis. Also, more or fewer than six laterally-extending irrigation channels may be present in the tip insert. Again, the outer surface of the tip insert may define a plurality of sensor ditches 76, and these ditches may be separated by a plurality of shell seats 78. These sensor ditches may be, for example, 0.010 inches deep. The shell seats, as described above, may be configured to ride against, or very near to, the inner surface of the conductive shell. A few of the sensor wire ramps are also clearly visible in FIG. 22. As previously described, the stem 74 of the tip insert may define a plurality of wire ditches 80 separated by a plurality of shank seats 82 as shown in FIG. 22.

Figure 23:
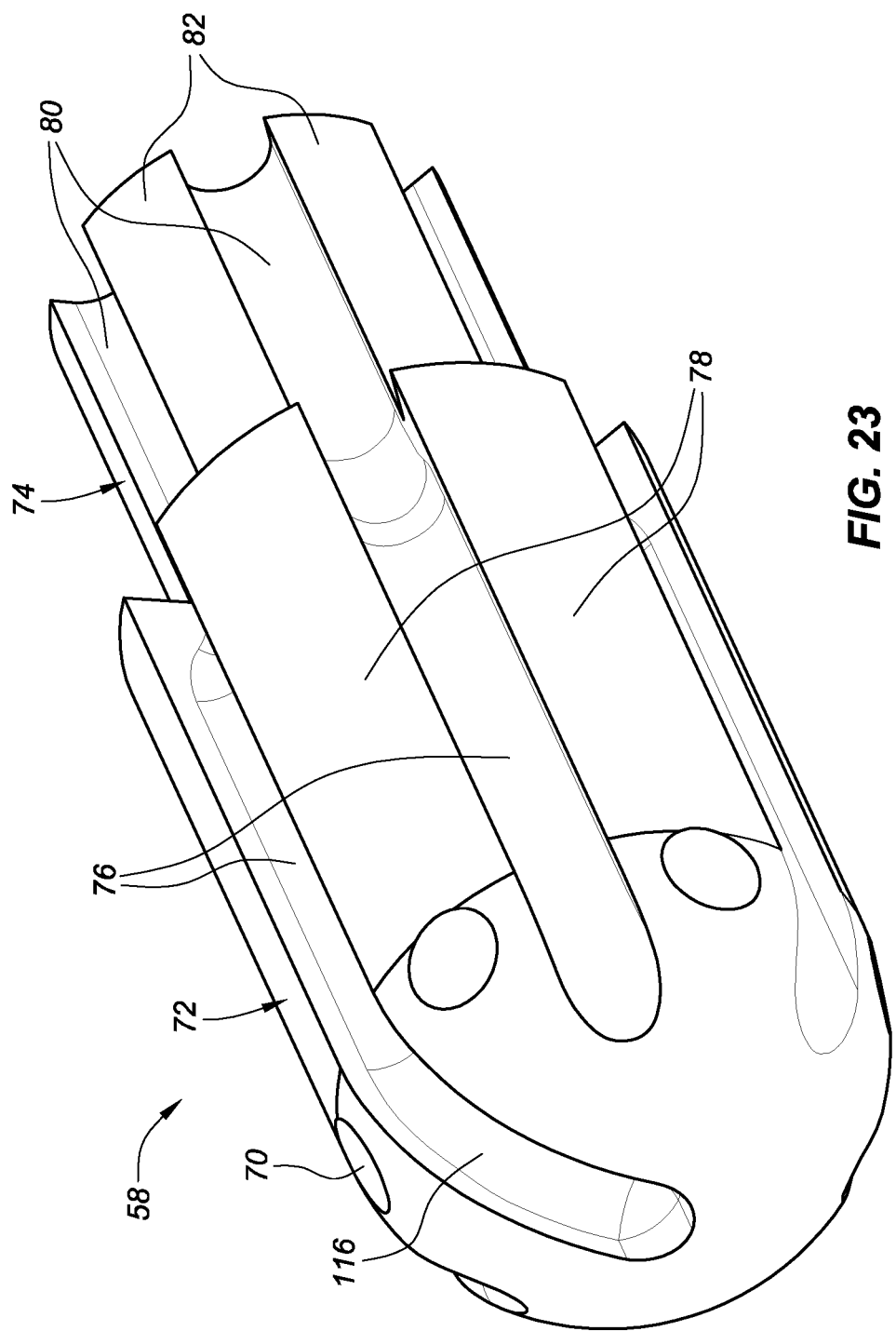
FIG. 23 depicts the tip insert of FIG. 22 in a slightly different angular orientation, revealing an arc-shaped channel or ditch that extends toward the distal end of the catheter tip to position the distal-most thermal sensor at that location.

FIG. 23 depicts the tip insert 58 of FIG. 22 in a slightly different orientation, revealing the arc-shaped channel 116 (or sensor ditch extension) that extends toward the distal-most end of the catheter tip to position the distal-most thermal sensor 114 (see, for example, FIG. 21) at that location. It should be kept in mind that this arc-shaped channel extension need not be present. It has been determined, however, that a number of advantages may be realized by positioning a thermal sensor as far distally on the catheter tip as possible. For example, in view of the rapid heat dissipation experienced by these catheter tips, it can be extremely helpful to sense temperature at this distal location since it may be in the best location for most accurately determining the temperature of the surrounding tissue during certain procedures.

Figure 24:
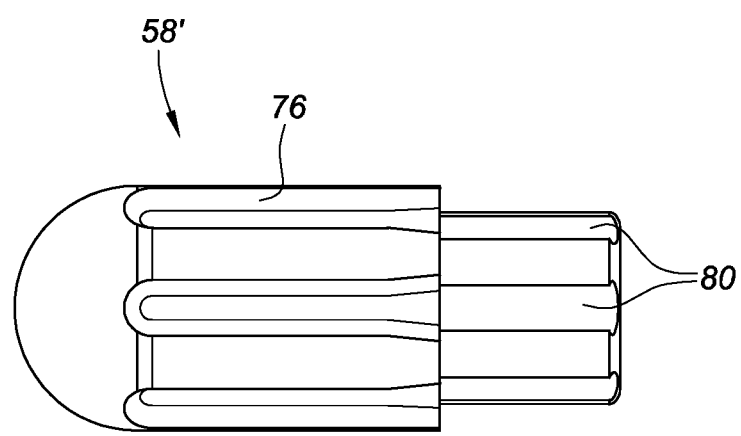
FIG. 24 depicts a thermally-insulative ablation tip insert for a non-irrigated embodiment of a catheter tip, such as the embodiment depicted in FIG. 9.

FIG. 24 depicts an alternative thermally-insulative ablation tip insert 58'. This tip insert could be used in a non-irrigated embodiment of the catheter tip 42', such as the embodiment depicted in FIG. 9. In particular, as discussed above, the control systems for delivering pulsed RF to ablation catheters described herein may completely eliminate the need for the use of irrigation. With that in mind, FIG. 24 depicts one possible configuration for a tip insert for use in a non-irrigated ablation catheter. This embodiment of the tip insert still includes sensor ditches 76 and sensor wire ditches 80 as described above.

Further, it should be understood that, in other embodiments of the thermally-insulative ablation tip insert (both irrigated and non-irrigated embodiments), there may be more or fewer sensor ditches 76. In fact, although the sensor ditches may facilitate placement of the sensors 68 on the insert (e.g., during catheter assembly), the outer surface of the main body of the tip insert may be smooth (or at least ditchless). In such an embodiment, the sensors may be aligned on the smooth outer surface of the tip insert (and, possibly, held in place by, for example, adhesive). Then, when the conductive shell is in place around the tip insert and the sensors 68 are in place between the outer surface of the tip insert and the inner surface of the conductive shell, the gaps or voids between the inner surface of the conductive shell and the outer surface of the tip insert may be filled with material (e.g., potting material or adhesive). It is worth noting that the sensors may be put in place before or after the conductive shell is placed over the tip insert. For instance, the sensors may be mounted on (e.g., adhered to) the smooth outer surface of the tip insert forming a tip-insert-sensor subassembly. Then, the conductive shell may be placed over that tip-insert-sensor subassembly before the remaining voids between the tip-insert-sensor subassembly and the conductive shell are filled. Alternatively, the conductive shell may be held in place over the tip insert while one or more sensors are slid into the gap between the outer surface of the tip insert and the inner surface of the conductive shell. Subsequently, the voids could again be filled. These alternative manufacturing techniques apply to all of the disclosed embodiments that comprise sensors mounted between a tip insert and a conductive shell member.

Figure 25:
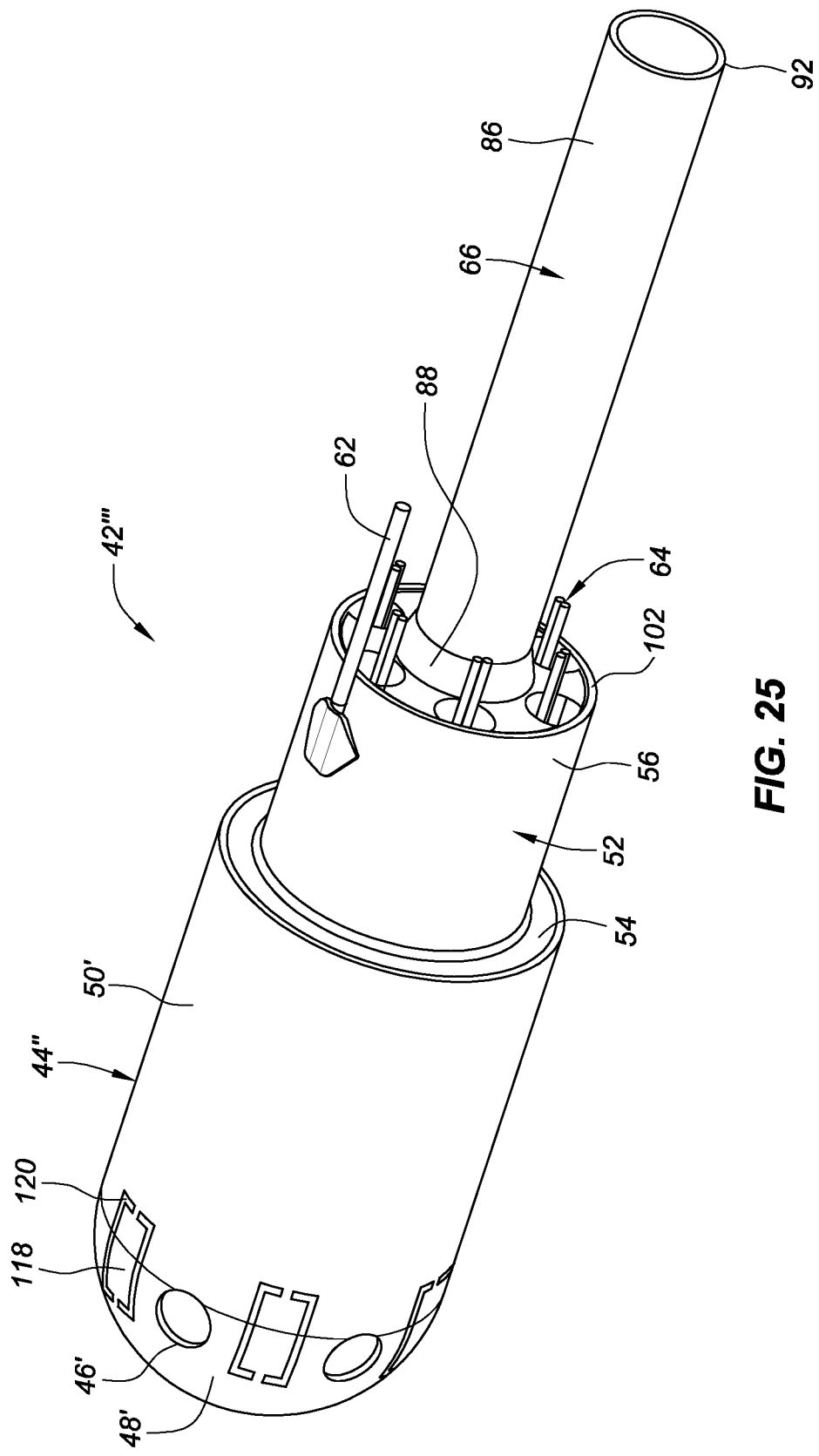
FIG. 25 is most similar to FIG. 8, but depicts an alternative embodiment comprising one or more isolated temperature-sensing islands.

FIG. 25 is most similar to FIG. 8, but depicts one form of an alternative embodiment of a catheter tip 42''' comprising one or more isolated temperature-sensing islands 118 which, in this embodiment, reside partially on the domed distal end 48' of the conductive shell 44'' and partially on the cylindrical body 50' of the conductive shell 44''. Each of these temperature-sensing islands 118 is outlined or circumscribed by a strip of insulative material 120 placed to reduce or eliminate any potential influence from irrigant flowing through the nearby holes 46' in the conductive shell. In particular, if the cooled irrigant flowing through a hole through the conductive shell meaningfully reduces the temperature of the conductive shell around the hole, that lower temperature would not be transmitted to a temperature sensor mounted within the conductive shell below the temperature-sensing island 118.

Although a single-layer conductive shell 44 (see, e.g., FIGS. 10-13 and 15) constructed from a thin layer of gold, for example, may perform in an magnetic resonance (MR) environment without causing undesirable or unmanageable MR artifacts, a conductive shell comprising an outer layer of a paramagnetic material such as platinum or platinum iridium, for example, may benefit from a multilayer construction as discussed below.

Figure 26:
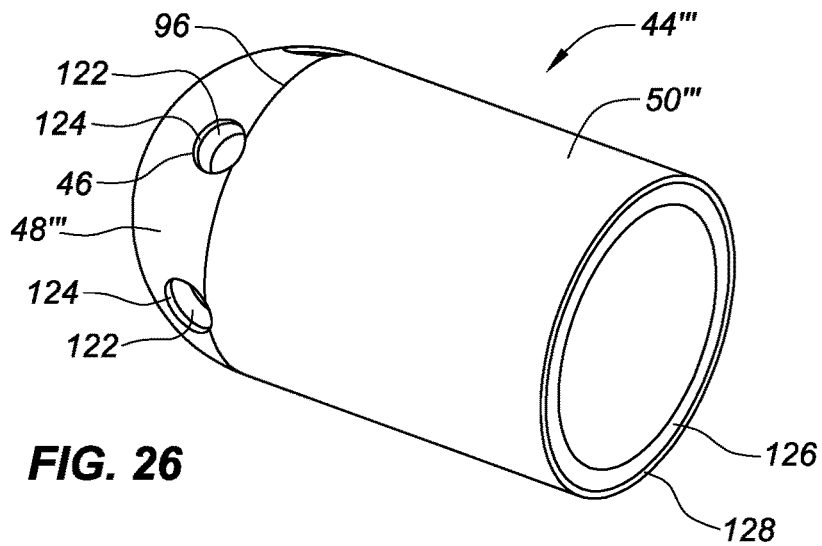
FIG. 26 is most similar to FIG. 12, but depicts a multilayer embodiment of the conductive shell.

FIG. 26 is most similar to FIG. 12, but depicts a multilayer conductive shell 44'''. A multilayer conductive shell may have just a multilayer cylindrical body portion, just a multilayer domed distal end portion, or both a multilayer domed distal end portion and a multilayer cylindrical body. In the embodiment depicted in FIG. 26, both the domed distal end portion 48''' and the cylindrical body 50''' have a multilayer construction. As shown in this figure, the domed distal end portion 48''' comprises an inner layer 122 and an outer layer 124, and the cylindrical body 50''' similarly comprises an inner layer 126 and an outer layer 128. Again, however, it is not a requirement that the domed distal end portion and the cylindrical body must both be constructed with the same number of layers or with the same thickness of layers. Also, the walls of the conductive shell 44''' may, for example, be of a total thickness that is the same as, or nearly the same as, the thickness 98 (see FIG. 12) of the single-layer conductive shell 44 described above. The conductive shell could be formed or manufactured per, for example, the techniques already described herein.

Figure 27A:
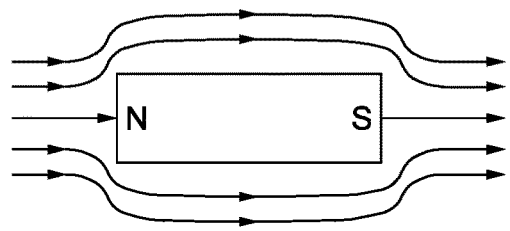
FIG. 27A schematically depicts magnetic flux lines reacting to a diamagnetic sub stance.
Figure 27B:
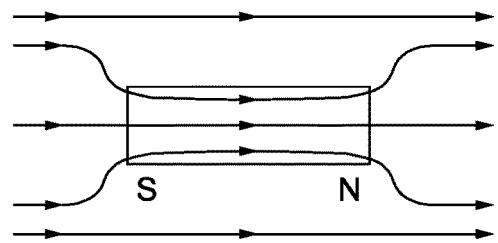
FIG. 27B schematically depicts magnetic flux lines reacting to a paramagnetic sub stance.
Figure 27C:
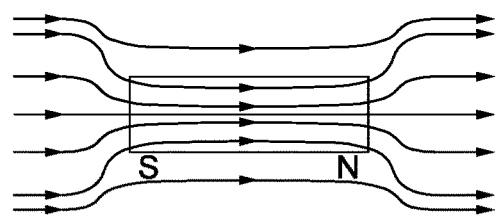
FIG. 27C schematically depicts magnetic flux lines reacting to a ferromagnetic sub stance.

FIGS. 27A, 27B, and 27C schematically depict various materials or substances in a magnetic field (e.g., in an MR environment). In particular, FIG. 27A schematically depicts magnetic flux lines reacting to a diamagnetic substance (the lines of force tend to avoid the substance when placed in a magnetic field), FIG. 27B schematically depicts magnetic flux lines reacting to a paramagnetic substance (the lines of force prefer to pass through the substance rather than air), and FIG. 27C schematically depicts magnetic flux lines reacting to a ferromagnetic substance (the lines of force tend to crowd into the substance). Platinum iridium (a paramagnetic material) is commonly used for constructing catheter tips. Thus, as may be discerned from looking at FIG. 27B, a thin conductive shell (e.g., conductive shell 44 depicted in FIG. 12) constructed entirely from platinum or platinum iridium (or some other paramagnetic material) may induce MR artifacts.

As mentioned above, a more MR compatible catheter tip may comprise, for example, a single layer conductive shell 44 constructed entirely from a diamagnetic material (e.g., a thin gold conductive shell) or a multilayer conductive shell 44'''. In one example of an MR compatible multilayer conductive shell, the conductive shell 44''' comprises a shell distal end portion (shown as domed distal end 48''' in FIG. 26) and a shell proximal end portion (shown as cylindrical body 50''' in FIG. 26). In this embodiment, the conductive shell 44''' may comprise a platinum iridium outer layer (or skin) 124, 128 and an inner layer (or liner or core) 122, 126 constructed from a diamagnetic material (e.g., gold or copper). In such an embodiment, the paramagnetic outer layer 124, 128 and the diamagnetic inner layer 122, 126 'cooperate' in a manner that minimizes or mitigates against the generation of undesirable MR artifacts. In some multilayer embodiments (e.g., with a paramagnetic outer layer and a diamagnetic inner layer), it can be beneficial to mass balance or volume balance the material comprising the layers of the multilayer conductive shell 44'''. Alternatively, the multilayer conductive shell 44''' of the MR compatible catheter tip may have an outer layer constructed from a diamagnetic material (such as bismuth or gold) and an inner layer constructed from a paramagnetic material (such as platinum or platinum iridium).

In yet another embodiment (not shown), a multilayer conductive shell may comprise more than two layers. For example, the conductive shell may comprise three layers, including a very thin outer layer of a paramagnetic material, a somewhat thicker or much thicker intermediate layer of a diamagnetic material, and an oversized internal layer of a non-precious metal (or plastic or other material) sized to ensure that the finished geometry of the overall ablation tip is of a desired size for effective tissue ablation.

Materials that could be used for the inner layer or liner include, but are not limited to, the following: silicon (metalloid); germanium (metalloid); bismuth (post transition metal); silver; and gold. Silver and gold are examples of elemental diamagnetic materials that have one-tenth the magnetic permeability of paramagnetic materials like platinum. Thus, one example multilayer shell configuration could comprise a platinum outer layer (or skin) and an inner layer (or liner or core) of gold or silver with a thickness ratio (e.g., platinum-to-gold thickness ratio) of at least $1/10$ (i.e., the platinum layer being one-tenth as thick as the gold layer). In another example, a multilayer conductive shell configuration 44''' could comprise a platinum outer layer and a bismuth inner layer with a thickness ratio (e.g., platinum-to-bismuth thickness ratio) of at least $1/2$ (i.e., the platinum outer layer being one-half as think as the bismuth inner layer) since bismuth has a permeability that is about one-half the permeability of platinum. The layers may also be constructed from alloys, which may be used, for example, when a pure element material might otherwise be disqualified from use in the construction of a catheter tip.

FIG. 28A is most similar to FIG. 20, but depicts an embodiment having both distal temperature or thermal sensors 68 and proximal temperature or thermal sensors 68' mounted on a tip insert. As depicted in FIG. 28A, a plurality of temperature sensors 68' may be deployed around or near the proximal end of the tip 42. These temperature sensors 68' could be mounted, for example, on the ablation tip insert as already described above. Although FIG. 28A depicts an ablation tip insert 58 for an irrigated tip 42, the proximal temperature sensors 68' may also be used in non-irrigated embodiments such as the tip 42' depicted in FIG. 9. The proximal thermal sensors 68' may be deployed, for example, in an angularly-spaced configuration similar to the configuration of the six radially-disposed distal temperature sensors 68 shown in, for example, FIGS. 15, 19, 20, and 21 (but located near the proximal end of the main body 72 of the ablation tip insert 58 rather than its distal end). The temperature sensor configuration depicted in FIG. 28A would provide a higher-resolution 'picture' of the thermal profile of the tip and, therefore, a better understanding of tissue temperature near the catheter tip during ablation. This is particularly beneficial when such a tip construction is used with the pulsed RF control systems disclosed herein.

As shown in FIG. 28A, a catheter tip consistent with the present disclosure may have one or more irrigant channels distributed along a length and around a circumference of the catheter tip. Various design factors including quantity, location, size, and nozzling effect (if any) of the irrigant channels may depend upon specific applications. In the present embodiment, six distal irrigation channels 70 are circumferentially distributed about a distal end of the ablation tip insert 58, with both distal thermocouples 68 and proximal thermocouples 68' located proximal thereof. Similarly, six proximal irrigation channels 70' are circumferentially distributed on a main body 72 of the ablation tip insert 58 near the intersection of the main body and stem 74. The proximal irrigation channels 70' are proximal of both distal thermocouples 68 and proximal thermocouples 68'.

FIG. 28B is an isometric view of a conductive shell 44 for assembly over the tip insert 58 of FIG. 28A, consistent with various aspects of the present disclosure. As shown in these figures, the conductive shell may comprise a hemispherical or nearly-hemispherical domed distal end 48 and a cylindrical body 50. In the figures, a 'seam' 96 is shown between the domed distal end 48 and the cylindrical body 50. This may be merely a circumferential transition line between the cylindrical body and the domed distal end of a unitary component; or, alternatively, it may be the location where the cylindrical body is connected to the domed distal end by, for example, welding. In one embodiment, the wall thickness 98 of the shell is 0.002 inches, but alternative wall thicknesses are also readily envisioned. The conductive shell 44 may be formed or manufactured by, for example, forging, machining, drawing, spinning, or coining. In this particular embodiment, the shell 44 includes 12 irrigation holes 46 and 46', six of which are visible in this isometric view. The irrigation holes form two circumferentially extending rings about the conductive shell. A first proximal circumferential ring including irrigation holes 46', and a second distal circumferential ring including irrigation holes 46. The 12 irrigation holes 46 and 46' align with the 12 irrigation channels 70 and 70' on the tip insert 58 (as shown in FIG. 28A). Although the conductive shell 44 depicted in the figures includes 12 irrigation holes 46 and 46', more or fewer holes may be used, and the size of the holes may be larger, or smaller, or a mix of larger and smaller holes.

Figure 29:
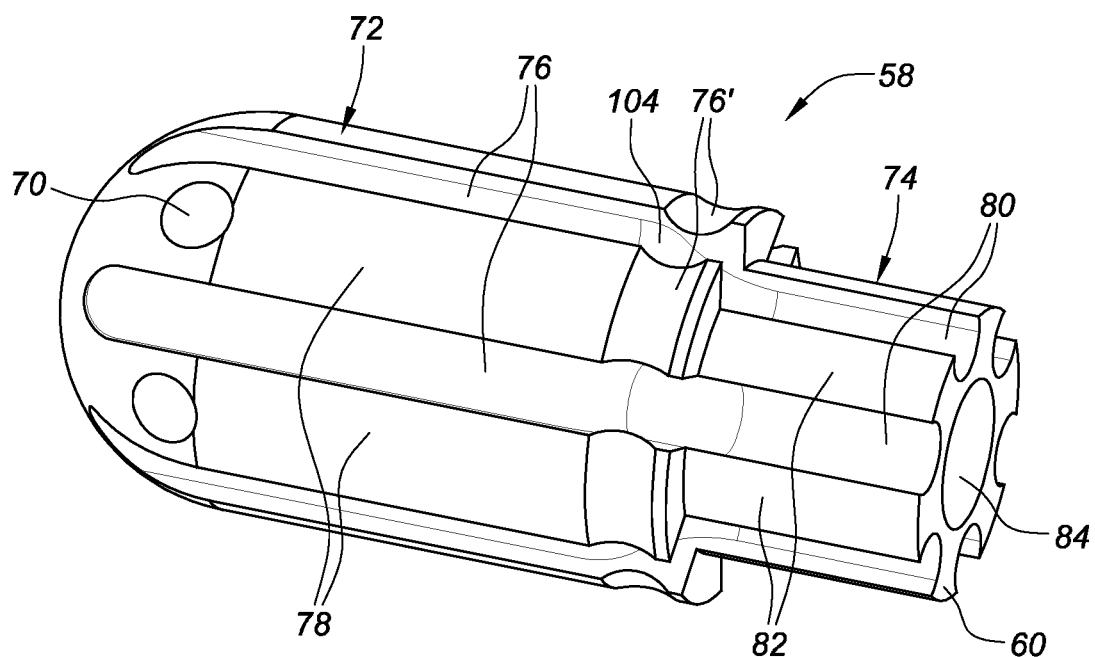
FIG. 29 is an isometric view of a thermally-insulative ablation tip insert including a radially extending channel or ditch, consistent with various aspects of the present disclosure.

FIG. 29 is an isometric view of a thermally-insulative ablation tip insert 58 including a plurality of longitudinally-extending channels or ditches 76, and a radially extending channel or ditch 76', consistent with various aspects of the present disclosure. The tip insert 58, which may be a unitary piece, includes a main body 72 and a stem 74. The thermally-insulative ablation tip insert 58 of FIG. 29 is shown without any other tip components. Various embodiments of the present disclosure are directed to the ablation tip insert 58 including (exclusively) thermally-insulative material, for example, ULTEM, plastic (such as PEEK, which is polyether ether ketone) or thermally-insulative ceramic. In the present embodiment, the tip insert 58 includes six radially-extending irrigation channels 70, each of the irrigation channels 70 extending substantially perpendicular to the longitudinal axis of a tube channel 84 (see, for example, FIG. 19) that is itself arranged substantially parallel to a longitudinal axis 94 (see, for example, FIG. 8). The laterally-extending irrigation channels 70 connect a distal end of the tube channel 84 to an outer surface of the tip insert. In various other embodiments, consistent with the present disclosure, the laterally-extending irrigation channels 70 can be arranged at a variety of angles relative to the longitudinal axis 94 of the catheter (i.e., different from 90°). Moreover, various embodiments may include more or fewer than six laterally-extending irrigation channels 70 in the tip insert 58.

In accordance with FIG. 29, an outer surface of tip insert 58 defines a plurality of longitudinally-extending sensor ditches 76 (relative to a longitudinal axis 94 of a catheter, as shown in FIG. 8) separated by a plurality of shell seats 78, and a radially-extending sensor ditch 76' near a proximal end of the main body 72. These sensor ditches may be, for example, 0.010 inches deep and house thermal sensors 68 and 68' therein (see, for example, FIG. 31). The shell seats 78 may be configured to ride against, or very near to, the inner surface of the conductive shell 44 (see, for example, FIG. 12). Accordingly, when the assembled tip insert 58, including thermocouples 68 and 68', is inserted into the conductive shell 44, the thermocouples are in close proximity or in direct contact with the conductive shell facilitating improved thermal response of the system.

A stem 74 of tip insert 58 may define a plurality of wire ditches 80 separated by a plurality of shank seats 82. In conjunction with the wire ditches 80, sensor ditches 76 and 76', and sensor wire ramps 104 extending between the sensor and wire ditches, wire leads extending from thermocouples coupled to the tip insert 58 may be routed back to a proximal end of a catheter shaft. In many embodiments, it may be desirable to route the wire leads in such a way as to prevent the wire leads from traversing underneath or around thermocouples within the sensor ditches 76 and 76', mitigating the potential for electrical interference between the wire leads and thermocouples. Specifically, in one embodiment, proximal thermal sensors may be fixed within a distal portion of longitudinally-extending sensor ditches 76, while distal thermal sensors may be radially offset from the proximal thermal sensors, and fixed within radially-extending sensor ditch 76'. This radial offset of the proximal and distal thermal sensors facilitates wire leads being run along a length of sensor ditch 76 without interfering with physical placement of the proximal thermal sensors therein—which may otherwise affect the relative contact of the proximal thermal sensors to the conductive shell 44 in final assembly.

It has been discovered, in accordance with the present disclosure, that deploying temperature sensors 68' (as shown in, for example, FIG. 31) around or near a proximal end of tip 42 in a radially-extending sensor ditch 76' facilitates improved thermal response. This is due to, at least in part, the proximity of the thermal sensors 68' to a conductive shell 44 when assembled. The precision of placement of the proximal thermal sensors 68' relative to conductive shell 44 is improved by the radially-extending sensor ditch 76'. Furthermore, an increased radial distance between the thermal sensors 68' within the radially-extending ditch 76' and a tube channel 84, that carries irrigant fluid to irrigation channels 70, helps to mitigate thermal sink there between that may impact the accuracy, and thermal response of the thermal sensors 68'.

Figure 30:
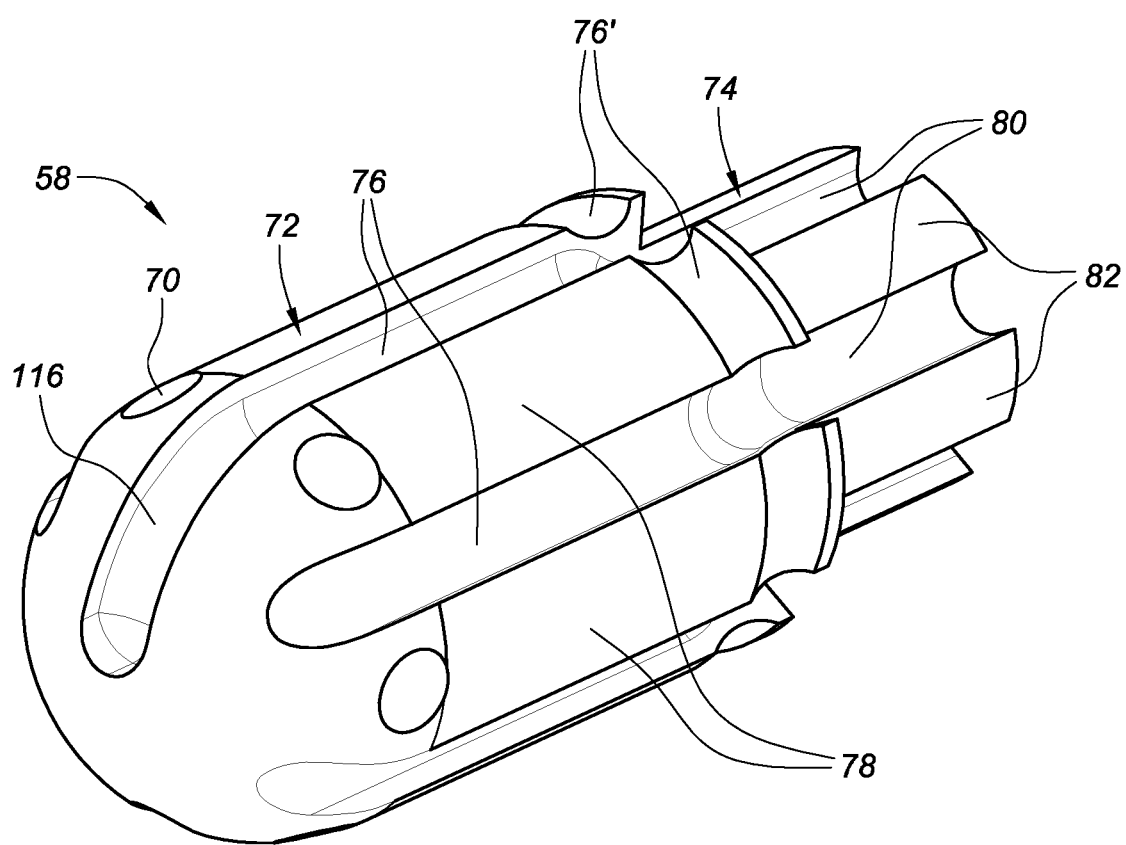
FIG. 30 depicts the tip insert of FIG. 29 in a slightly different angular orientation, revealing an arc-shaped channel or ditch that extends toward a distal end of the catheter tip to position a distal-most thermal sensor at that location, consistent with various aspects of the present disclosure.

FIG. 30 depicts the tip insert of FIG. 29 in a slightly different angular orientation, revealing an arc-shaped channel or ditch 116 that extends from one of the longitudinally-extending sensor ditches 76 toward a distal end of the catheter tip to position a distal-most thermal sensor 114 (see, for example, FIG. 21) at that location, consistent with various aspects of the present disclosure. While some embodiments of the present disclosure need not include such an arc-shaped channel extension 116, a number of advantages may be realized by positioning a thermal sensor as far distally on the catheter tip as possible. Specifically, due to the rapid heat dissipation experienced by such catheter tips, a thermal sensor at the distal tip (within arc-shaped channel extension 116) may provide the most accurate temperature reading of tissue surrounding the distal tip of the catheter during certain procedures. For example, in many applications of an ablation therapy the distal tip of the catheter may be in contact with target tissue.

Figure 31:
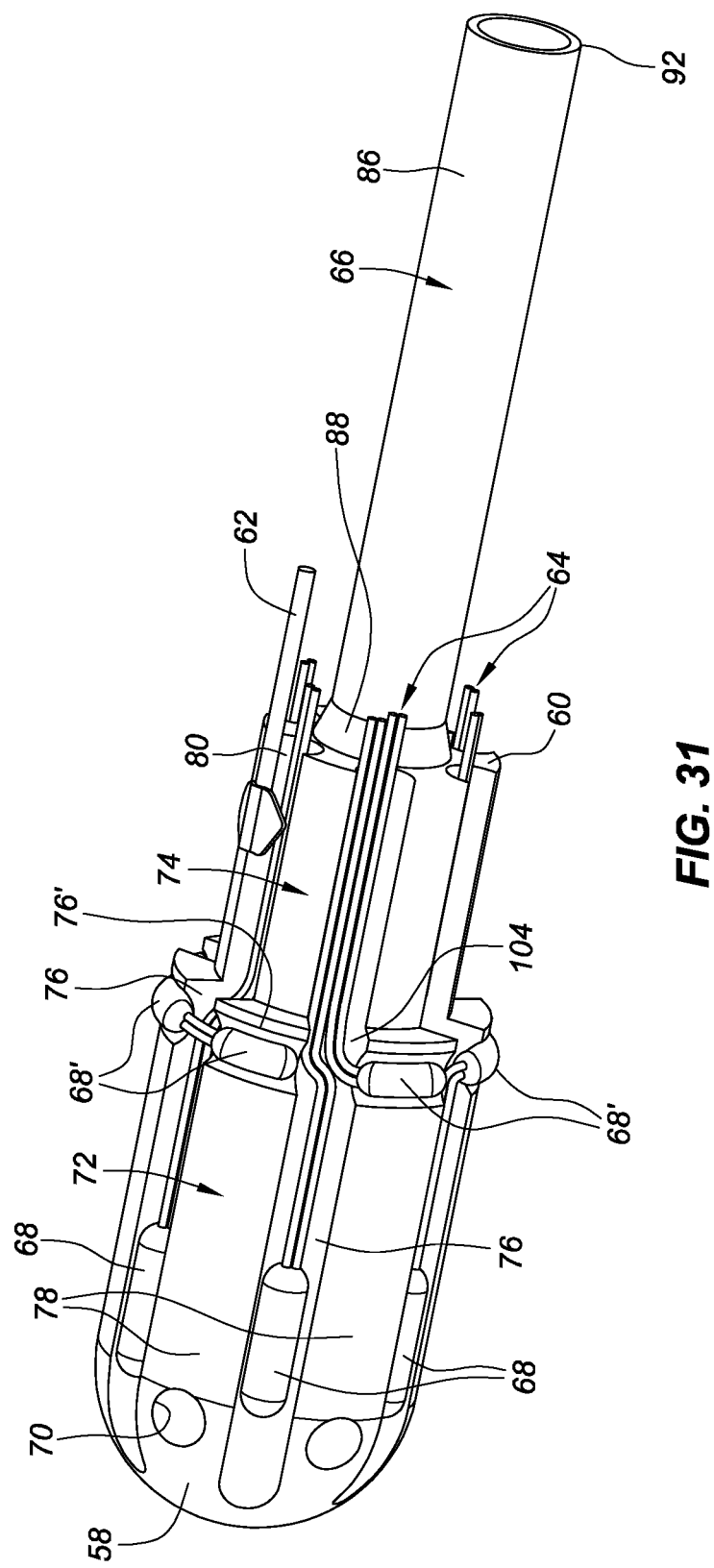
FIG. 31 depicts an embodiment of a tip insert, as shown in FIGS. 29, and 30, on which both distal and proximal temperature sensors are mounted, consistent with various aspects of the present disclosure.

FIG. 31 depicts an embodiment of a tip insert 58, as shown in FIGS. 29, and 30, on which both distal and proximal temperature sensors (68 and 68', respectively) are mounted, consistent with various aspects of the present disclosure. In this figure, all six of the radially-disposed thermal sensors 68 are positioned in their respective longitudinally-extending sensor ditches 76. The seventh, distal-most thermal sensor may be positioned within arc-shaped channel extension 116 (see, for example, FIG. 30), but is not shown in this particular figure. FIG. 31 also depicts a frustoconical boss comprising part of the optional seating sleeve 88 with its distally-facing surface or tip resting against the proximally-facing surface 60 of tip insert 58.

FIG. 31 depicts an embodiment having both distal temperature sensors 68 and proximal temperature sensors 68' mounted on tip insert 58. As depicted in FIG. 31, the plurality of proximal temperature sensors 68' may be deployed around or near the proximal end of the tip 42. These proximal temperature sensors 68' may be mounted, for example, within radially-extending sensor ditch 76' near a proximal end of the ablation tip insert 58. The radially-extending sensor ditch 76' may house one or more proximal temperature sensors 68'. These temperature sensors 68' may either be longitudinally aligned with the respective sensor ditches 76 (and distal temperature sensors 68), or radially offset relative to the sensor ditches 76. When the proximal temperature sensors 68' are radially offset from the distal temperature sensors 68, as shown in FIG. 31, lead wire pairs 64 from each of the proximal and distal temperature sensors may be run in such a way as to prevent the lead wire pairs and another temperature sensor from coming into contact or otherwise affecting the other temperature sensor (e.g., electromagnetic interference). Specifically, a lead wire pair 64 extending from distal temperature sensor 68 extends through longitudinally-extending sensor ditch 76, and through wire ditch 80 to a proximal end of the catheter shaft. As the proximal temperature sensors 68' are radially offset from the distal temperature sensors, the lead wire pair 64 extending from the distal temperature sensor 68 does not physically or electrically interact with the proximal temperature sensor 68'. Similarly, a lead wire pair 64 extending from proximal temperature sensor 68' extends through a short portion of the radially-extending sensor ditch 76' before running along the longitudinally-extending sensor ditch 76, and through the wire ditch 80 to the proximal end of the catheter shaft.

Although FIG. 31 depicts an ablation tip insert 58 for an irrigated tip 42, such a configuration including proximal temperature sensors 68' in a radially-extending sensor ditch 76' may also be used in non-irrigated embodiments such as the tip 42' depicted in FIG. 9. The temperature sensor configuration depicted in FIG. 31 would provide a higher-resolution 'picture' of the thermal profile of the tip and, therefore, a better understanding of tissue temperature near the catheter tip during an ablation therapy. This is particularly beneficial when such a tip construction is used with a pulsed RF control system as disclosed herein.

Figure 32:
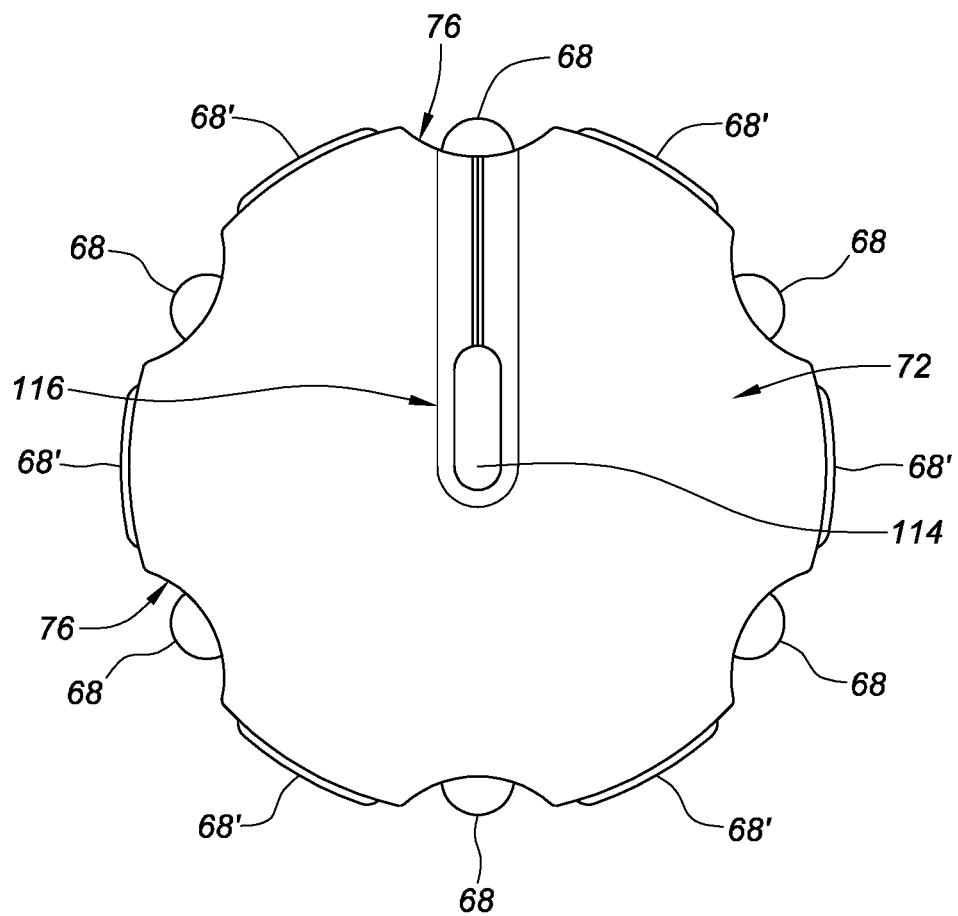
FIG. 32 depicts a front view of the tip insert of FIG. 31, revealing the distal-most thermal sensor, consistent with various aspects of the present disclosure.

FIG. 32 depicts a front view of a tip insert 58 of FIG. 31, revealing the distal-most thermal sensor 114 which extends to the distal end of the tip insert within an arc-shaped channel extension 116, consistent with various aspects of the present disclosure. The present view also further exemplifies the radially offset nature of distal temperature sensors 68 relative to proximal temperature sensors 68'. Not only does the proximal and distal thermal sensors' locations along the length and circumference of the longitudinal axis of the tip insert facilitate enhanced temperature resolution across a length of the tip insert, but also an enhanced radial temperature resolution around the circumference of the tip insert. As a result, the present embodiment displays enhanced temperature resolution and sensitivity that enables the ablation catheter to contact and ablate tissue anywhere along conductive shell 44 (as shown in FIG. 16, for example), but also to accurately control the ablation based on one or more of the temperature sensors—such as the temperature sensor in closest proximity to the tissue being ablated. Moreover, in more specific/detailed embodiments, consistent with the present disclosure, a temperature sensor configuration including proximal and distal temperature sensors (68' and 68, respectively) also facilitates identification of a contact zone between the conductive shell 44 and tissue. In such an embodiment, during an ablation therapy the warmest temperature reading of the temperature sensor may be indicative of contact with tissue as the remaining sensors (and the portion of the conductive shell 44 in contact therewith) experience significant thermal sync from the blood pool.

Figure 33:
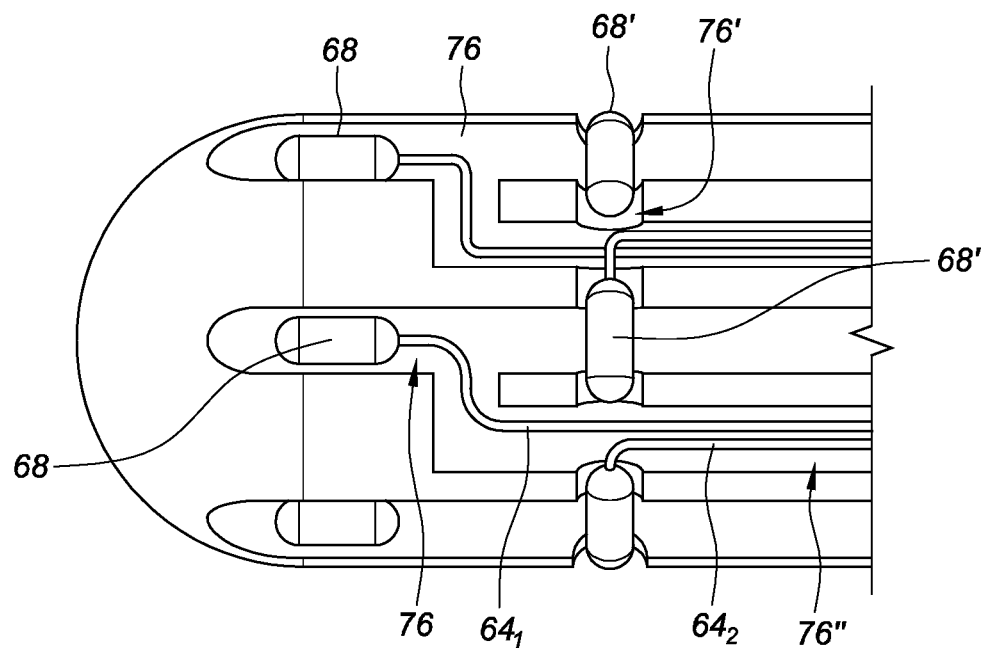
FIG. 33 is a side view of one exemplary configuration of a tip insert including various catheter tip components, consistent with various aspects of the present disclosure.

FIG. 33 is a side view of one exemplary configuration of a tip insert including various catheter tip components, consistent with various aspects of the present disclosure. Specifically, a thermal sensor configuration is depicted that facilitates longitudinal alignment of distal thermal sensors 68 and proximal thermal sensors 68' while mitigating interaction between lead wire pair $64_1$ (extending from the distal thermal sensors 68) and proximal thermal sensors 68'. As discussed above, running the lead wire pair $64_1$ along the same longitudinally-extending sensor ditch 76 that a proximal thermal sensor 68' is placed within may affect the thermal coupling between the proximal thermal sensor 68' and a conductive shell 44 (as shown in FIG. 16, for example). Moreover, the lead wire pairs 64 may emit electromagnetic interference that inhibits the accuracy (or other desirable characteristic) of the proximal thermal sensors 68', or vice versa. Accordingly, the present embodiment further includes a longitudinally-extending lead wire ditch 76" that extends between adjacent longitudinally-extending sensor ditches 76. The lead wire pairs $64_1$ that extend from distal thermal sensors 68 are diverted from the longitudinally-extending sensor ditches 76 to the longitudinally-extending lead wire ditches 76" prior to reaching the proximal thermal sensors 68'. As the proximal thermal sensors 68' are longitudinally aligned with the distal thermal sensors 68, lead wire pairs $64_2$ that extend from the proximal thermal sensors 68' (within radially-extending sensor ditches 76') may similarly be diverted into the longitudinally-extending lead wire ditches 76", whereby both sets of lead wire pairs $64_{1-2}$ then extend to the proximal end of the catheter shaft.

Figure 34:
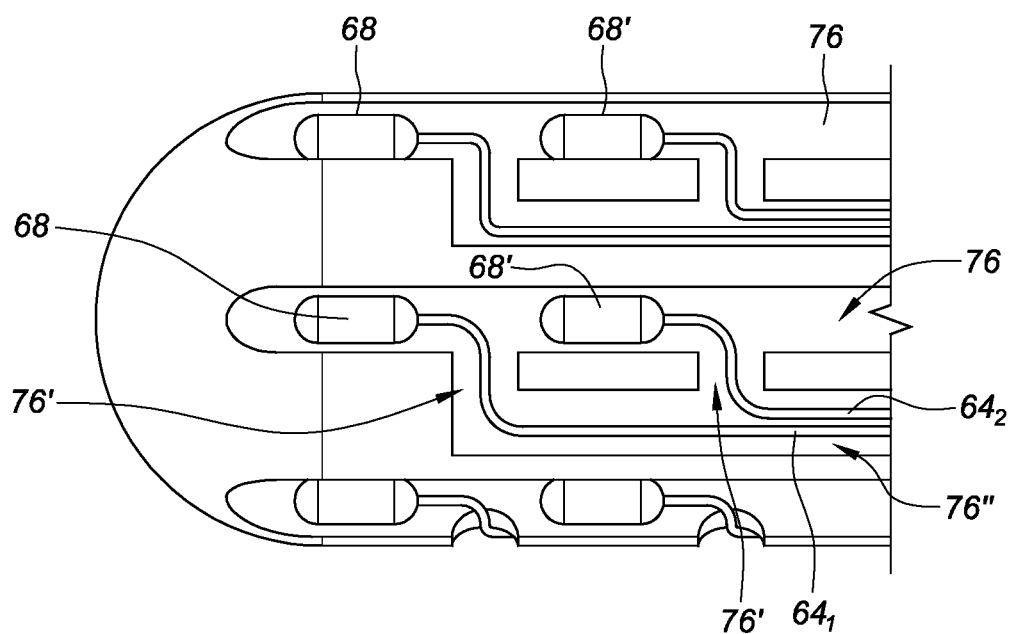
FIG. 34 is a side view of another exemplary configuration of a tip insert including various catheter tip components, consistent with various aspects of the present disclosure.

FIG. 34 is a side view of another exemplary configuration of a tip insert including various catheter tip components, consistent with various aspects of the present disclosure. Specifically, a thermal sensor configuration is depicted that facilitates longitudinal alignment of distal thermal sensors 68 and proximal thermal sensors 68' within the same longitudinally-extending sensor ditch 76, while mitigating interaction between lead wire pair $64_1$ (extending from the distal thermal sensors 68) and proximal thermal sensors 68'. To prevent such interaction, the present embodiment further includes a longitudinally-extending lead wire ditch 76" that extends between adjacent longitudinally-extending sensor ditches 76. Lead wire pairs $64_1$ extend from distal thermal sensors 68 and are diverted from the longitudinally-extending sensor ditches 76 to the longitudinally-extending lead wire ditches 76", via a distal radially-extending ditch 76' prior to reaching the proximal thermal sensors 68'. Similarly, lead wire pairs $64_2$ extend from the proximal thermal sensors 68' and may be diverted into the longitudinally-extending lead wire ditches 76" via a proximal radially-extending ditch 76'. Both sets of lead wire pairs $64_{1-2}$ then extend together to the proximal end of the catheter shaft. In other embodiments, the lead wire pairs $64_2$ may extend from the proximal thermal sensors 68' to the proximal end of the catheter shaft along the longitudinally-extending sensor ditch 76, independent of the lead wire pairs $64_1$.

Figure 35:
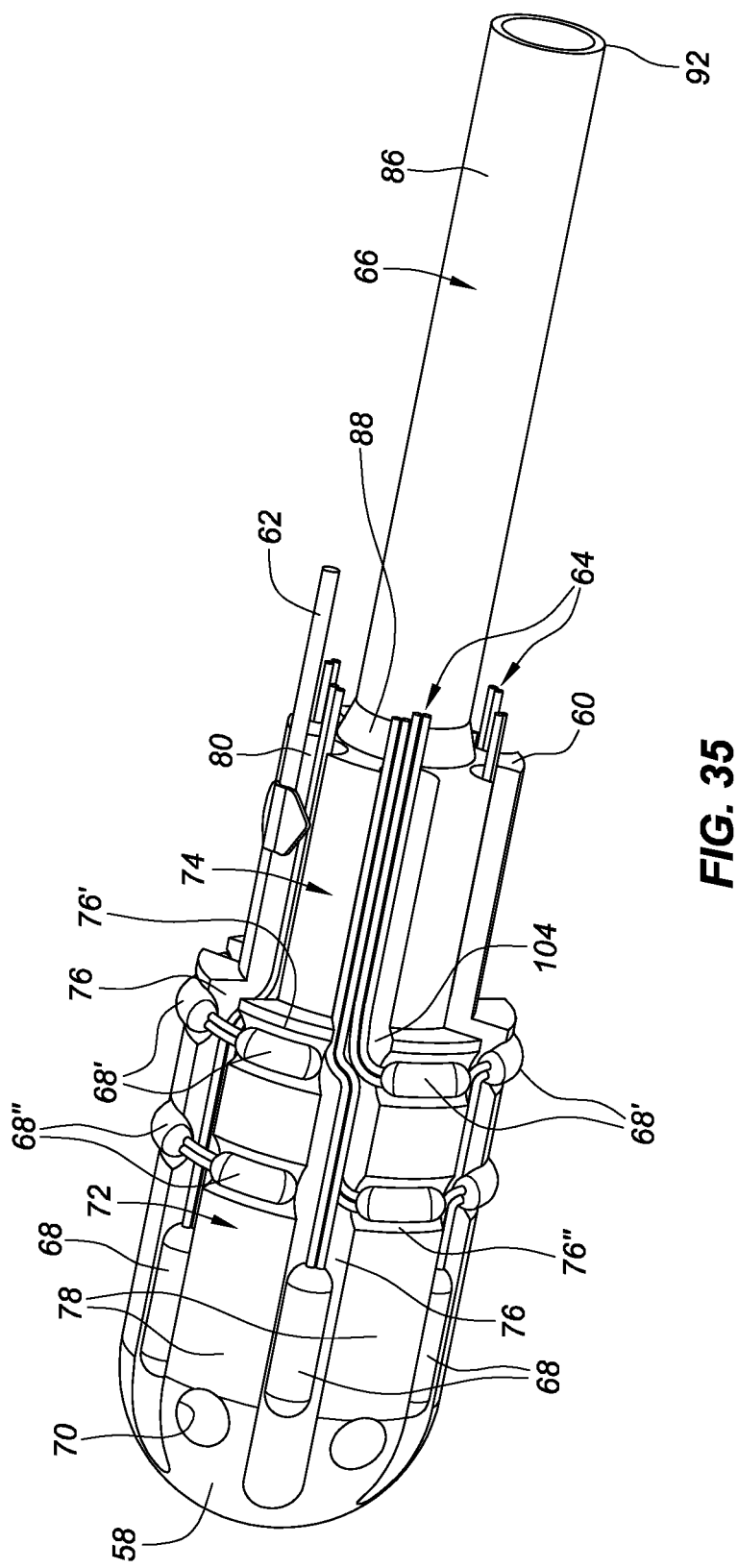
FIG. 35 depicts an embodiment of a tip insert including a plurality of longitudinally-extending channels or ditches, and two longitudinally offset, radially extending channels or ditches on which both distal, proximal, and intermediate temperature sensors are mounted, consistent with various aspects of the present disclosure.

FIG. 35 depicts an embodiment of a tip insert 58 including two longitudinally offset, radially-extending channels or ditches (76' and 76") on which both proximal, and intermediate thermal sensors (68' and 68", respectively) are mounted, consistent with various aspects of the present disclosure. In this figure, thermal sensors 68 are positioned in their respective sensor ditches 76. Another, distal-most thermal sensor 114 may be positioned within arc-shaped channel extension 114 (see, for example, FIG. 21), but is not shown in this particular figure. FIG. 35 also depicts a frustoconical boss comprising part of the optional seating sleeve 88 with its distally-facing surface or tip resting against the proximally-facing surface 60 of tip insert 58.

FIG. 35 further depicts an embodiment having both distal thermal sensors 68, proximal thermal sensors 68', and intermediate thermal sensors 68" mounted on tip insert 58. As depicted in FIG. 35, a plurality of proximal thermal sensors 68' may be deployed around or near the proximal end of the tip insert 58. Specifically, the proximal thermal sensors 68' may be mounted, for example, within a first radially-extending sensor ditch 76' on the ablation tip insert 58. The first radially-extending sensor ditch 76' may house one or more proximal thermal sensors 68', these thermal sensors 68' may either be radially aligned with the respective sensor ditches 76, or radially offset relative to the sensor ditches 76. When the proximal thermal sensors 68' are radially offset from the distal thermal sensors 68, as shown in FIG. 35, lead wire pairs 64 from each of the proximal and distal thermal sensors may be run in such a way as to prevent the lead wire pairs from another thermal sensor from coming into contact or otherwise affecting (e.g., electromagnetic interference) another thermal sensor. Specifically, a lead wire pair 64 extending from distal thermal sensor 68 extends through longitudinally-extending sensor ditch 76, and through wire ditch 80 to a proximal end of the catheter shaft. As the proximal thermal sensors 68' are radially offset from the distal thermal sensors, the lead wire pairs 64 extending from the distal thermal sensors 68 do not physically or electromagnetically interact with the proximal thermal sensors 68'. Similarly, a lead wire pair 64 extending from proximal thermal sensors 68' extend through a short portion of the first radially-extending sensor ditch 76' before running along the longitudinally-extending sensor ditch 76 (proximal of distal thermal sensor 68), and through the wire ditch 80 to the proximal end of the catheter shaft.

The embodiment of FIG. 35 further includes a second radially-extending sensor ditch 76" distal of a first radially-extending sensor ditch 76'. The second radially-extending sensor ditch 76" may house one or more intermediate thermal sensors 68". These intermediate thermal sensors 68" may either be axially aligned with the respective sensor ditches 76, or radially offset relative to the sensor ditches. When the intermediate thermal sensors 68" are radially offset from the distal thermal sensors 68, as shown in FIG. 35, lead wire pairs 64 from each of the proximal, distal, and intermediate thermal sensors may be run in such a way as to prevent the lead wire pairs from coming in close proximity to the other thermal sensors. As discussed above, contact between lead wire pairs and thermal sensors may impact the thermal coupling between the thermal sensors and a conductive shell 44 (as shown in FIG. 16, for example) which encompasses the tip insert 58. Moreover, contact between lead wire pairs and thermal sensors may result in electromagnetic interference across the thermal sensor signals potentially corrupting signal data.

By positioning each of the thermal sensors 68, 68', and 68" within a ditch, the thermal sensors may be precisely positioned in contact with (or in close proximity to) a conductive shell once assembled. This precise positioning of the thermal sensors facilitates a comparable thermal response across all of the thermal sensors which is desirable for consistent control inputs during an ablation therapy, for example.

Although FIG. 35 depicts an ablation tip insert 58 for an irrigated tip 42, such a configuration including proximal thermal sensors 68' in a radially-extending sensor ditch 76' may also be used in non-irrigated embodiments, such as the tip 42' depicted in FIG. 9. By adding a third row of thermal sensors 68" in a second radially-extending sensor ditch 76", a higher-resolution 'picture' of the thermal profile of the tip may be achieved. This may be particularly beneficial when such a tip construction is used with a pulsed RF control system as disclosed herein.

Catheter tips having a variety of thermometry configurations could be deployed successfully with the pulsed RF control systems described herein. Thus, although the representative catheter tips described herein include six or twelve radially-disposed thermal sensors and one distal thermal sensor placed close to the distal end of the catheter tip, the invention is not limited to such seven-sensor and thirteen-sensor configurations.

Also, catheters comprising various segmented tip designs may work to good advantage with the control systems described above. Some such tip configurations are disclosed in U.S. patent application No. 61/896,304, filed 28 Oct. 2013, and in related international patent application no. PCT/US2014/062562, filed 28 Oct. 2014 and published 7 May 2015 in English as international publication no. WO 2015/065966 A2, both of which are hereby incorporated by reference as though fully set forth herein.

It should also be noted that the control systems described herein may use a "rolling thermocouple," which would, for example, measure the temperature output from each of a plurality of thermocouples every 20 msec (for example) and report the highest of these temperatures to the pulse control box and, potentially, directly to the generator (at least for safety shutdown reasons). In this manner, and in view of the low thermal mass of the ablation tips described herein, the controller is always working with the most accurate representation of the actual tissue temperature. In particular, since the device has low thermal mass, any temperature sensors facing away from the tissue during use of the catheter in an ablation procedure would cool rapidly and their readings could be ignored or discounted, whereas the temperature sensor or sensors closest to the portion of the catheter tip that is in contact with tissue would heat rapidly and would, therefore, provide a temperature reading that is closest to the actual temperature of the tissue being ablated. Thus, by using only the temperature reading from the hottest temperature sensor (or the two or three hottest temperature sensors) at any given time, the system is able to rapidly adjust for the widely varying readings being received from the thermal sensors as the catheter tip is rotated or pushed into tissue during actual use.

Although several embodiments have been described above with a certain degree of particularity, those skilled in the art could make numerous alterations to the disclosed embodiments without departing from the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A high-thermal-sensitivity ablation catheter tip, the tip comprising:
    an electrically-conductive housing comprising a conductive shell;
    a thermally-insulative tip insert, wherein the conductive shell surrounds at least a portion of the tip insert, and the thermally-insulative tip insert includes a plurality of longitudinally-extending sensor channels and a radially-extending sensor channel;
    a plurality of thermal sensors in thermal communication with the conductive shell and configured to provide directional temperature feedback, wherein the plurality of thermal sensors comprise thermal sensors distributed around the tip insert in the plurality of longitudinally-extending sensor channels and the radially-extending sensor channel; and
    a wired or wireless communication pathway communicatively connected to the plurality of thermal sensors and configured to report the directional temperature feedback to an ablation control system.

2. The high-thermal-sensitivity ablation catheter tip of claim 1, wherein the thermal sensors are circumferentially distributed around the tip insert in the plurality of longitudinally-extending sensor channels are radially offset relative to the thermal sensors that are circumferentially distributed around the tip insert in the radially-extending sensor channel.

3. The high-thermal-sensitivity ablation catheter tip of claim 2, wherein the radial offset of the thermal sensors that are circumferentially distributed around the tip insert in the plurality of longitudinally-extending sensor channels and the thermal sensors that are circumferentially distributed around the tip insert in the radially-extending sensor channel is approximately 30 degrees.

4. The high-thermal-sensitivity ablation catheter tip of claim 1, wherein the wired or wireless communication pathway includes a plurality of lead wires extending from each of the thermal sensors and in a proximal direction along at least one of the plurality of longitudinally-extending sensor channels, and wherein the thermal sensors are positioned within the plurality of longitudinally-extending sensor channels and the radially-extending sensor channel to mitigate contact between the thermal sensors and the plurality of lead wires.

5. The high-thermal-sensitivity ablation catheter tip of claim 1, wherein the thermal sensors are circumferentially distributed around the tip insert in the plurality of longitudinally-extending sensor channels are longitudinally offset relative to the thermal sensors that are circumferentially distributed around the tip insert in the radially-extending sensor channel.

6. The high-thermal-sensitivity ablation catheter tip of claim 1, the thermally-insulative tip insert further includes a plurality of longitudinally-extending lead wire channels positioned between each of the plurality of longitudinally-extending sensor channels, the wired or wireless communication pathway includes a plurality of lead wires extending from the thermal sensors, and the longitudinally-extending lead wire channels are configured and arranged to receive the plurality of lead wires extending from the plurality of thermal sensors and to mitigate electromagnetic interference between the thermal sensors and the lead wires by routing the lead wires along the longitudinally-extending lead wire channels, separate from the thermal sensors in the longitudinally-extending sensor channels.

7. The high-thermal-sensitivity ablation catheter tip of claim 1, wherein the thermally-insulative tip insert further includes a second radially-extending sensor channel positioned longitudinally distal from the radially-extending sensor channel, and at least a portion of the thermal sensors are circumferentially distributed around the tip insert in the second radially-extending sensor channel.

8. The high-thermal-sensitivity ablation catheter tip of claim 1, wherein the conductive shell further comprises an inner surface, and wherein the plurality of thermal sensors are in thermal communication with the inner surface of the conductive shell.

9. The high-thermal-sensitivity ablation catheter tip of claim 1, wherein the plurality of thermal sensors further comprises a distal-most thermal sensor positioned at or near a distal-most end of the conductive shell.

10. An ablation tip for an ablation catheter, the ablation tip comprising:
    a thermally and electrically conductive housing comprising a conductive shell that comprises an inner surface;
    a thermally-insulative tip insert, wherein the conductive shell surrounds at least a portion of the tip insert, and the thermally-insulative tip insert includes a plurality of longitudinally-extending sensor channels and a plurality of longitudinally-extending lead wire channels positioned between the plurality of longitudinally-extending sensor channels;
    a plurality of thermal sensors are circumferentially distributed around the tip insert in the plurality of longitudinally-extending sensor channels and in thermally-transmissive contact with the inner surface of the conductive shell, wherein the plurality of thermal sensors are configured to receive and report temperature feedback received via the conductive shell; and
    a wired or wireless communication pathway communicatively connected to the plurality of thermal sensors and configured to facilitate reporting of the temperature feedback to an ablation control system.

11. The ablation tip for an ablation catheter of claim 10, wherein the plurality of thermal sensors are circumferentially distributed around the tip insert in the plurality of longitudinally-extending sensor channels in a proximal circumferential ring and a distal circumferential ring, wherein the proximal circumferential ring is longitudinally offset relative to the distal circumferential ring, and the wired or wireless communication pathway further includes a plurality of lead wires extending from each of the thermal sensors, the plurality of lead wires extending from the thermal sensors in the distal circumferential ring are routed along at least one of the plurality of longitudinally-extending lead wire channels.

12. The ablation tip for an ablation catheter of claim 11, wherein the plurality of lead wires extending from the thermal sensors in the proximal circumferential ring are routed along at least one of the plurality of longitudinally-extending lead wire channels.

13. The ablation tip for an ablation catheter of claim 10, wherein the plurality of thermal sensors mounted on the tip insert are in physical contact with the inner surface of the conductive shell.

14. The ablation tip for an ablation catheter of claim 10, wherein at least two of the plurality of thermal sensors are mounted in one of the plurality of longitudinally-extending sensor channels.

15. An ablation catheter tip having high-thermal-sensitivity, the tip comprising:
 a thermally-insulative ablation tip insert comprising a first portion and a second portion, wherein the first portion of the tip insert comprises a plurality of longitudinally-extending sensor channels and a radially-extending sensor channel, and the insert is configured and arranged to support a plurality of temperature sensors circumferentially distributed around the tip insert in the plurality of longitudinally-extending sensor channels and the radially-extending sensor channel, and where the temperature sensors form proximal and distal circumferential rings, and;
 a conductive shell comprising a shell distal end portion and a shell proximal end portion, wherein the conductive shell is adapted to fit around the first portion of the insert in thermally-conductive contact with the plurality of temperature sensors in the proximal and distal circumferential rings; and
 a shank adapted to cover the second portion of the insert, whereby the conductive shell and the shank are conductively connected and together effectively encase the ablation tip insert.

16. The ablation catheter tip of claim 15, wherein the temperature sensors that are circumferentially distributed around the ablation tip insert in the plurality of longitudinally-extending sensor channels are radially offset relative to the thermal sensors that are circumferentially distributed around the tip insert in the radially-extending sensor channel.

17. The ablation catheter tip of claim 15, the thermally-insulative ablation tip insert further includes a plurality of longitudinally-extending lead wire channels positioned between the plurality of longitudinally-extending sensor channels, the wired or wireless communication pathway includes a plurality of lead wires, and the lead wire channels are configured and arranged to receive lead wires extending from the thermal sensors and to mitigate electromagnetic interference between the thermal sensors and the lead wires extending therefrom.

18. The ablation catheter tip of claim 15, wherein the thermally-insulative ablation tip insert further includes a plurality of longitudinally-extending shell seats, each of the longitudinally-extending shell seats separating adjacent longitudinally-extending sensor channels.

19. The ablation catheter tip of claim 15, wherein one of the plurality of longitudinally-extending sensor channels further comprises an arc-shaped channel extension, and wherein the plurality of temperature sensors comprises a distal-most thermal sensor positioned at a distal-most portion of the ablation catheter tip.

20. The ablation catheter tip of claim 15, wherein the ablation catheter tip further comprises at least one isolated temperature-sensing island in thermally-transmissive contact with the at least one temperature sensor, and wherein each temperature-sensing island is circumscribed by a strip of insulative material.

* * * * *